US00RE41943E

(19) United States
(12) Reissued Patent
Held et al.

(10) Patent Number: US RE41,943 E
(45) Date of Reissued Patent: Nov. 16, 2010

(54) GLYPHOSATE-RESISTANT PLANTS

(75) Inventors: Bruce Held, Ames, IA (US); Herbert Wilson, Ames, IA (US); Philip E. Dykema, Ames, IA (US); Carol J. Lewnau, Ames, IA (US); Janelle C. Eby, Ames, IA (US)

(73) Assignee: Mertec, LLC, West Point, IA (US)

(21) Appl. No.: 12/633,520

(22) Filed: Dec. 8, 2009

Related U.S. Patent Documents

Reissue of:
(64) Patent No.: 7,045,684
Issued: May 16, 2006
Appl. No.: 10/223,241
Filed: Aug. 19, 2002

(51) Int. Cl.
*A01H 5/00* (2006.01)
*C12N 15/82* (2006.01)

(52) U.S. Cl. ..... 800/300; 435/419; 435/468
(58) Field of Classification Search ..... None
See application file for complete search history.

(56) References Cited

U.S. PATENT DOCUMENTS

| | | | |
|---|---|---|---|
| 4,535,060 | A | 8/1985 | Comai |
| 4,769,061 | A | 9/1988 | Comai |
| 4,940,835 | A | 7/1990 | Shah |
| 5,310,667 | A | 5/1994 | Eichholtz |
| 5,491,288 | A | 2/1996 | Chaubet |
| 5,510,471 | A | 4/1996 | Lebrun |
| 5,554,798 | A | 9/1996 | Lundquist |
| 5,633,448 | A | 5/1997 | Lebrun |
| RE36,449 | E | 12/1999 | Lebrun |
| 6,040,497 | A | 3/2000 | Spencer |
| 7,626,077 | B2 | 12/2009 | Held |

FOREIGN PATENT DOCUMENTS

| | | | |
|---|---|---|---|
| WO | WO9506128 | A2 | 3/1996 |
| WO | WO9704103 | A2 | 2/1997 |
| WO | GB2326163 | A | 12/1998 |
| WO | WO0066748 | A1 | 11/2000 |

OTHER PUBLICATIONS

Richmond and Somerville 2000, Plant Physiology vol. 124, pp. 495–498.
Klee et al. 1986, Mol. Gen. Genet. 210:437–442.
Benefy et al. 1988 The Plant Cell 2:849–856.
Richmond et al. "The cellulose synthase superfamily" Plant Physiology, vol. 124, pp. 495–498 Oct. 2000.
Ruff et al "Effects of amino acid substitutions on glyphosate tolerance and activity of EPSPS Synthase" Plant Physiology, vol. 96 (Supp. 1) p. 94, 1991.
Ku et al, Jan. 1999, Nature Biotechnology vol. 17, pp. 76–80.
Rose et al., Mar. 2008, The Plant Cell. vol. 20 pp. 543–551.
Green 2009 Weed Science 57:108–117.
Hernandez–Garcia et al. "A soybean (glycine max) polyubiquitin promoter gives strong constitutive expression in transgenic soybean" Plant Cell REp (2009) 28:837–849.

*Primary Examiner*—David H Kruse

(57) ABSTRACT

This invention relates to glyphosate-resistant transgenic plants and methods of making the same. In a preferred embodiment, a DNA fragment which comprises an EPSPS 5' regulatory sequence and a glyphosate-resistant EPSPS coding sequence is introduced into regenerable plant cells. The encoded EPSPS has a chloroplast transit peptide. The DNA fragment does not contain a non-EPSPS enhancer. Cells are selected for stable transformation, and the selected cells can be used to regenerate glyphosate-resistant transgenic plants. The DNA fragment used for transformation preferably comprises a modified plant genomic sequence, such as SEQ ID NO: 2, SEQ ID NO:4 or SEQ ID NO: 6. In one embodiment, two DNA fragments of this invention are stably transformed into a plant to confer glyphosate-resistance.

13 Claims, No Drawings

GLYPHOSATE-RESISTANT PLANTS

Matter enclosed in heavy brackets [ ] appears in the original patent but forms no part of this reissue specification; matter printed in italics indicates the additions made by reissue.

TECHNICAL FIELD

This invention relates to glyphosate-resistant transgenic plants and methods of making the same.

BACKGROUND

Glyphosate is a widely used component in herbicides. Glyphosate inhibits 5-enolpyruvyl-3-phosphoshikimic acid synthase (EPSP synthase, or EPSPS), which is involved in the synthesis of aromatic amino acids in plant cells. Inhibition of EPSPS effectively disrupts protein synthesis and thereby kills the affected plant cells. Because glyphosate is non-selective, it kills both weeds and crop plants. Accordingly, there is a need to produce transgenic crop plants that are resistant to glyphosate.

Recombinant DNA technology has been used to create mutant EPSP synthases that are glyphosate-resistant. These mutant EPSP synthases can be transformed into plants and confer glyphosate-resistance upon the transformed plants. Examples of mutant EPSP synthases and glyphosate-resistant transgenic plants are illustrated in U.S. Pat. Nos. 6,040,497 and 5,554,798, 5,310,667 and WO 00/66748.

Current plant transformation technology employs chimeric expression vectors. These vectors include regulatory sequences, such as enhancers or promoters, that are heterologous to the EPSPS genes. For instance, WO 00/66748 fuses enhancers from CaMV 35S, FMV 35S, rice actin 1, rice GOS2, maize polyubiquitin, or barley plastocyanin genes to a glyphosate-resistant EPSPS coding sequence in order to enhance the expression of the glyphosate-resistant EPSPS in transformed plant cells.

No one has used a complete expression cassette of the EPSP synthase gene isolated from the genome of a donor plant and mutated to give glyphosate resistance. In one embodiment of the present invention, the expression cassette of the EPSP synthase gene consists of a native EPSPS 5' regulator sequence, a coding sequence (with or without introns) encoding a glyphosate-resistant EPSPS which includes a native transit peptide, and a native EPSPS 3' regulatory sequence (such as an EPSPS transcriptional terminator). The fact that such an expression cassette is sufficient to provide glyphosate resistance is surprising. Moreover, the use of the native EPSPS 5' and/or 3' regulatory sequences simplifies the process of constructing expression vectors suitable for plant transformation.

Suitable sources of EPSP synthase genes include dicotyledonous plants, such as Arabidopsis thaliana, and monocotyledonous plants, such as Zea mays, Arabidopsis thaliana has two EPSP synthase genes (epm1 and epm2). The present invention includes use of one or both of mutated epm1 and epm2 to confer resistance to glyphosate. Mutated EPSP synthase genes from Zea mays or other plants can also be used for transforming plant cells to make glyphosate-resistant plants.

SUMMARY OF THE INVENTION

In accordance with one aspect of the present invention, a DNA fragment which comprises an EPSPS 5' regulatory sequence and a glyphosate-resistant EPSPS coding sequence (including a chloroplast transit peptide coding sequence) is introduced into regenerable plant cells. The DNA fragment does not contain a non-EPSPS enhancer. Cells are selected for stable transformation. The selected cells are then used to regenerate glyphosate-resistant, transgenic plants.

In one embodiment, the DNA fragment used for transformation comprises a modified plant genomic sequence. The unmodified plant genomic sequence comprises at least part of an EPSPS gene, and includes an EPSPS 5' regulatory sequence and a glyphosate-sensitive EPSPS coding sequence (including a chloroplast transit peptide coding sequence). The glyphosate-sensitive EPSPS coding sequence is modified to make the encoded EPSPS glyphosate-resistant. The DNA fragment comprising the modified plant genomic sequence is stably transformed into plant cells, from which glyphosate-resistant plants are regenerated.

In a preferred embodiment, the DNA fragment used for transformation comprises SEQ ID NO: 2. In another preferred embodiment, the DNA fragment used for transformation comprises SEQ ID NO: 4. In yet another preferred embodiment, the DNA fragment comprises SEQ ID NO: 6. In a further preferred embodiment, any two sequences selected from SEQ ID. NO: 2, SEQ ID NO: 4, and SEQ ID NO: 6 are used to transform plant cells. In one embodiment, the transgenic plant comprises transformed SEQ ID. NO: 2 and SEQ ID NO: 4.

Other features, objects, and advantages of the present invention are apparent in the detailed description that follows. It should be understood, however, that the detailed description, while indicating preferred embodiments of the invention, are given by way of illustration only, not limitation. Various changes and modifications within the spirit and scope of the invention will become apparent to those skilled in the art from the detailed description.

DETAILED DESCRIPTION

This invention relates to methods of making glyphosate-resistant plants. In accordance with one aspect of the invention, a DNA fragment is introduced into regenerable, glyphosate-sensitive recipient plant cells. The DNA fragment comprises an EPSPS 5' regulatory sequence, and a coding sequence encoding a glyphosate-resistant EPSPS. The EPSPS 5' regulatory sequence is operably linked to the EPSPS coding sequence. The glyphosate-resistant EPSPS includes a chloroplast transit peptide. The DNA fragment does not contain a non-EPSPS enhancer. The recipient plant cells are selected for glyphosate-resistance and stable transformation. The cells thus selected can be used to regenerate glyphosate-resistant plants. As used herein, a "DNA fragment" may be either linear or circular. Preferably, the DNA fragment used for transformation is a linear DNA fragment. A "coding sequence" encoding an EPSPS refers to a nucleic acid sequence transcription and translation of which produce a functional EPSPS. The boundaries of the coding sequence are generally determined by a translation start codon at its 5' end and a translation stop co don at its 3, end. A coding sequence of EPSPS may be a cDNA, or a plant genomic sequence which consists of all of the exons and introns of an EPSPS gene. An EPSPS gene refers to the plant genomic sequence which includes the EPSPS 5' regulatory sequence, the EPSPS coding sequence (including the sequence encoding the chloroplast transit peptide), and the EPSPS 3' regulatory sequence (such as an EPSPS transcriptional terminator). A "plant genomic sequence" refers to a nucleotide sequence found in the genome of the plant.

A chloroplast transit peptide functions post-translationally to direct a polypeptide to chloroplast. Either endogenous or heterologous chloroplast peptides can be used in the present invention. As used herein, "heterologous" means derived from a different source, and "endogenous" means derived from the same source. In a preferred embodiment, the endogenous transit peptide encoded by a native EPSPS gene is used.

As used herein, an EPSPS 5' regulatory sequence refers to a nucleotide sequence located upstream (5') to the start codon of the EPSPS coding sequence in an EPSPS gene in a plant or plant cell which has not been subject to genetic engineering. The 5' regulatory sequence generally includes an EPSPS promoter which directs the transcription of the EPSPS gene. Preferably, the EPSPS 5' regulatory sequence comprises one or more EPSPS enhancers operably linked to the promoter. In one embodiment, the 5' regulatory sequence comprises at least 200 bp. Preferably, the 5' regulatory sequence comprises at least 400, 600, 800, 1000, 1,200 or 1,800 bp.

An EPSPS 3' regulatory sequence refers to a nucleotide sequence located downstream (3') to the stop codon of the EPSPS coding sequence in an EPSPS gene in a plant or plant cell which has not been subject to genetic engineering. The 3, regulatory sequence generally includes a transcription terminator which controls the termination of the transcription of the EPSPS gene.

"Operably linked" refers to a juxtaposition of genetic elements, wherein the elements are in a relationship permitting them to operate in the expected manner. For instance, a 5' regulatory sequence is operably linked to a coding sequence if the 5' regulatory sequence functions to initiate transcription of the coding sequence.

Preferably, the DNA fragment used for transformation does not include a non-EPSPS enhancer. As used in the present invention, a "non-EPSPS enhancer" refers to an enhancer which is not used by an EPSPS gene in a plant or plant cell which has not been subject to genetic engineering. Non-EPSPS enhancers include, but are not limited to, enhancers that are associated with CaMV 35S, FMV 35S, rice actin 1, rice GOS2, maize polyubiquitin, or barley plastocyanin genes.

As used herein, a "glyphosate-resistant" cell or plant refers to a cell or plant that can survive or continue to grow in the presence of certain concentrations of glyphosate that typically kill or inhibit the growth of other cells or plants. Growth includes, for instance, photosynthesis, increased rooting, increased height, increased mass, or development of new leaves. In one embodiment, a glyphosate-resistant cell can grow and divide on a culture medium containing 50 mg/l or more glyphosate. Preferably, a glyphosate-resistant cell can grow and divide on a culture medium containing 100 mg/l or more glyphosate, such as 200 mg/l, 300 mg/l or 400 mg/l glyphosate. More preferably, a glyphosate-resistant cell can grow and divide on a culture medium containing 500 mg/l or more glyphosate, such as 600 mg/l. For purposes of the present invention, the term "glyphosate" includes any herbicidally effective form of N-phosphonomethylglycine (including any salt thereof) and other forms which result in the production of the glyphosate anion in plants.

Regenerable glyphosate-resistant plant cells may be used to regenerate glyphosate-resistant plants. In one embodiment, the glyphosate-resistant plant thus regenerated can survive or continue to grow after being sprayed with glyphosate at a rate of 25 g/ha (grams per hectare) or more. Preferably, the glyphosate-resistant plant thus regenerated can survive or continue to grow after being sprayed with glyphosate at a rate of 50 g/ha or more, such as 100 g/ha, 200 g/ha, 400 g/ha, or 800 g/ha. More preferably, the glyphosate-resistant plant thus regenerated can survive or continue to grow after being sprayed with glyphosate at a rate of 1000 g/ha or more, such as 2000 g/ha and 3000 g/ha. The spray may preferably be carried out at or after the growth stage of v2, such as v3, v4, v5 or later stages. In another embodiment, the regenerated glyphosate-resistant plant can tolerate the spray of glyphosate at between 0.1 M and 0.4 M.

As used herein, a "glyphosate-resistant" EPSPS refers to an EPSPS the expression of which in a plant cell confers glyphosate resistance upon the plant cell. An EPSPS is "glyphosate-sensitive" if it does not confer glyphosate-resistance when being expressed in plant cells.

A variety of EPSPS mutations have been known to be glyphosate-resistant and capable of conferring glyphosate resistance upon transformed plants. For instance, EPSPS of Zea mays (GenBank Accession No. X63374) can be mutated at amino acid residues 102 (substitution of He for Thr) and 106 (substitution of Ser for Pro). EPSPS encoded by epm1 gene of Arabidopsis thaliana can be mutated at amino acid residues 179 (substitution of He for Thr) and 183 (substitution of Ser for Pro). EPSPS encoded by epm2 gene of Arabidopsis thaliana can be mutated at amino acid residues 177 (substitution of He for Thr) and 182 (substitution of Ser for Pro). These mutated EPSPSs are glyphosate-resistant and capable of conferring glyphosate resistance upon transformed plants. Other mutated or modified EPSPSs, such as those described in U.S. Pat. Nos. 5,310,667, 5,866,775, 6,225,114, and 6,248,876, or natural EPSPS variants showing glyphosate-resistance, can be used in the present invention. In addition, bacteria-derived, glyphosate-resistant EPSPSs, after fusion with a chloroplast transit peptide, can also be used.

The DNA fragment comprising the EPSPS 5' regulatory sequence and the glyphosate-resistant EPSPS coding sequence can be stably transformed into a regenerable plant cell. As used herein, stable transformation refers to integration of the DNA fragment into the genome of the transformed plant cell.

In one embodiment, the EPSPS 5' regulatory sequence in the DNA fragment used for transformation comprises an EPSPS enhancer and an EPSPS promoter. In another embodiment, the DNA fragment used for transformation further comprises an EPSPS 3' regulatory sequence, such as an EPSPS transcriptional terminator, which is operably linked to the coding sequence encoding the glyphosate-resistant EPSPS.

In yet another embodiment, the DNA fragment used for transformation comprises a modified plant genomic sequence that encodes a glyphosate-resistant EPSPS. Without modification, the plant genomic sequence encodes a glyphosate-sensitive EPSPS. Modifications that are capable of converting a glyphosate-sensitive EPSPS to a glyphosate-resistant EPSPS are known in the art.

In a preferred embodiment, the DNA fragment used for transformation is modified from a plant genomic sequence. Before modification, the plant genomic sequence comprises an EPSPS regulatory sequence, a coding sequence encoding a glyphosate-sensitive EPSPS which includes a chloroplast transit peptide, and preferably an EPSPS 3, regulatory sequence, such as an EPSPS transcriptional terminator. The genomic sequence may be obtained by fragmenting the genome of a plant of interest, or isolated from bacterial artificial chromosome clones. Other methods for obtaining genomic sequences can also be used, such as PCR or DNA synthesis.

The EPSPS-coding sequence in this plant genomic sequence is then subject to nucleotide modification(s) to render the encoded EPSPS glyphosate resistant. Suitable modifications for this purpose, such as nucleotide substitutions, are well known in the art. The DNA fragment comprising the genomic sequence thus modified can be stably transformed into glyphosate-sensitive recipient plant cells. These transformed plant cells are selected for glyphosate resistance and then used to regenerate glyphosate-resistant plants.

The recipient plant cells are regenerable. They can be derived from immature embryos or meristematic tissues which contain cells that have not yet terminally differentiated. Juvenile leaf basal regions, immature tassels and gametic cells can be used to provide regenerable recipient cells for Zea mays. The preferred source of recipient cells for soybean includes the immature cotyledon.

In another preferred embodiment, two or more DNA fragments can be stably transformed into a recipient plant cell. Each of these DNA fragments includes an EPSPS 5' regulatory sequence, a coding sequence encoding a glyphosate-resistant EPSPS which contains a chloroplast transit peptide, and preferably an EPSPS 3' regulatory sequence (such as an EPSPS transcriptional terminator). These DNA fragments can be modified plant genomic sequences. They can be derived from the same or different plant species. They can be derived from the same EPSPS gene, or from different EPSPS genes of the same plant species, such as emp1 and emp2 of Arabidopsis thaliana.

Transformation of plant cells can be carried out using various methods. These methods include, but are not limited to, Agrobacterium tumefaciens mediated DNA transfer, PEG or liposome mediated DNA transfer, electroporation, microinjection, microprojectile or particle bombardment, receptor-mediated DNA transfer, and viral or other vector mediated DNA transfer. Preferably, transformation is carried out using aerosol beam injection as described in U.S. patent application Ser. No. 09/450,226, which is incorporated herein by reference.

Selection for stably transformed plant cells can be performed using methods as appreciated by one of ordinary skill in the art. For instance, the transformed cells can be grown and selected on media containing glyphosate. Preferably, the introduced DNA fragment is stably transformed and integrated into a chromosome of the transformed plant cell. A variety of assays can be used to confirm stable transformation. Suitable assays include molecular biological assays, such as Southern and Northern Blotting and PCR, or biochemical assays, such as ELISA and Western Blot. In addition, plant part assays, such as leaf and root assays, or analysis of the phenotype of the whole regenerated plant, can be used to confirm stable transformation.

Plants can be regenerated from the selected, stably transformed cells. Progeny can be recovered from the regenerated plants and tested for glyphosate resistance. Seeds or other parts of the regenerated transgenic plants can also be obtained. In one embodiment, glyphosate-resistant plants are made by crossing.

Both monocotyledonous and dicotyledonous plants can be transformed using the methods of the present invention. The glyphosate-resistant EPSPS coding sequence can be derived from either monocotyledonous or dicotyledonous plants. The representative monocotyledonous and dicotyledonous plants used in the present invention include, but are not limited to, Oryza sativa, Zea mays, Hordeum vulgare, Triticum aestivum, Avena sativa, turf grasses including species of the genera Poa, Festuca, Lolium, Zoysia, and Cynodon among others, Glycine max, Gossypium hirsutii, Lycopersicum esculentum, Solanum tuberosum, Phaseolus species, Beta vulgaris, and Brassica species.

Unless defined otherwise, all technical and scientific terms used herein have the same meaning as commonly understood by one of ordinary skill in the art to which this invention belongs. Generally, the nomenclature used herein and the laboratory procedures in cell culture and molecular genetics described herein are those well known and commonly employed in the art. Standard techniques can be used for recombinant nucleic acid methods, polynucleotide synthesis, plant cell culture, cell culture, tissue culture, and plant transformation and regeneration. Generally, enzymatic reactions and purification and/or isolation steps are performed according to the manufacturers' specifications. The techniques and procedures are generally performed according to conventional methodology disclosed, for example, in Molecular Cloning A Laboratory Manual, 2d ed., Cold Spring Harbor Laboratory Press, Cold Spring Harbor, N.Y. (1989), and Current Protocols in Molecular Biology (John Wiley & Sons, Baltimore, Md., 1989).

It should be understood that the above-described embodiments and the following examples are given by way of illustration, not limitation. Various changes and modifications within the spirit and scope of the present invention will become apparent to those skilled in the art from the present description.

EXAMPLE 1

Preparation and Mutation of Arabidopsis Genomic Fragments Containing EPSPS Genes Two bacterial artificial chromosome (BAC) clones, F27K7 and F4L23, were obtained from the Arabidopsis Biological Resource Center, DNA Stock Center, at the Ohio State University. F27K7 and F4L23 contain the EPSPS genes found on chromosome 1 and 2 of Arabidopsis thaliana, respectively. The F27K7 clone was digested using Sac II and Bam HI restriction enzymes to produce a 4.7 kb fragment, the sequence of which is shown as SEQ ID NO: 1. The 4.7 kb fragment comprises the complete EPSPS gene (epm1) found on chromosome which includes an EPSPS 5' regulatory sequence (the sequence before nucleotide residue 1290), an EPSPS coding sequence (from nucleotide residue 1290 to nucleotide residue 3729), and an EPSPS 3, regulatory sequence (the sequence after nucleotide residue 3729). The EPSPS coding sequence also encodes a chloroplast transit peptide (from nucleotide residue 1290 to nucleotide residue 1612). The sequence encoding this chloroplast transit peptide can be predicted using the computer program PSORT maintained on the public accessible GenomeNet at Kyoto University, Japan.

The 4.7 kb fragment was cloned into a pbluescript II vector (Stratagene), and two nucleotide substitutions were introduced into the EPSPS coding sequence using QuikChange® Site-Directed Mutagenesis Kit (Stratagene) according to the instructions of the manufacturer. The two nucleotide substitutions are a cytosine to thymine substitution at nucleotide 2007 and a cytosine to thymine substitution at nucleotide 2018. The mutated sequence is shown as SEQ ID NO: 2. The mutated sequence encodes a glyphosate-resistant EPSPS which has, as compared to the EPSPS encoded by SEQ ID NO: 1, a Thr to Ile mutation at amino acid 179 and a Pro to Ser mutation at amino acid 183. The amino acid sequence of the glyphosate-resistant EPSPS is shown as SEQ ID NO: 7. The pbluescript II vector containing SEQ ID NO: 2 is referred to as epm1 vector.

The BAC F4L23 clone was digested using Eco RI restriction enzyme to produce a 5.2 kb fragment, the sequence of which is shown as SEQ ID NO: 3. The 5.2 kb fragment comprises the complete EPSPS gene (epm2) from chromosome 2, which includes an EPSPS 5 'regulatory sequence (the sequence before nucleotide 1515), and EPSPS coding sequence (from nucleotide 1515 to nucleotide 3872), and an EPSPS 3' regulatory sequence (the sequence after nucleotide 3872). The EPSPS coding sequence also encodes a chloroplast transit peptide (from nucleotide 1515 to nucleotide 1665). The sequence encoding this chloroplast transit peptide can be predicted using the computer program PSORT maintained on the public accessible GenomeNet at Kyoto University, Japan.

The 5.2 kb fragment was cloned into a pbluescript II vector, and then subject to site-directed mutagenesis using QuikChange® Site-Directed Mutagenesis Kit (Stratagene). SEQ ID NO: 4 shows the mutated sequence which has two nucleotide substitutions in the EPSPS coding sequence as compared to SEQ ID NO: 3. The two substitutions are a cytosine to thymine substitution at nucleotide 2134 and a cytosine to thymine substitution at nucleotide 2145. The mutated sequence encodes a glyphosate-resistant EPSPS which has, as compared to the EPSPS encoded by SEQ ID NO: 3, a Thr to Ile mutation at amino acid 178 and a Pro to Ser mutation at amino acid 182. The amino acid sequence of the (*putative*) glyphosate-resistant EPSPS is shown as SEQ ID: 8. The pbluescript II vector containing SEQ ID NO: 4 is referred to as epm2 vector.

EXAMPLE 2

Transformation of Soybean

The Bam HI/Sac II fragment (SEQ ID NO: 2) of epm1 vector and the Eco RI fragment (SEQ ID NO: 4) of epm2 vector were used to transform soybean embryogenic callus using an aerosol beam injector as described in U.S. patent application Ser. No. 09/450,226, which is incorporated herein by reference. These fragments comprised mutant epm1 and mutant epm2 which encode (*putative*) glyphosate-resistant EPSPSs. These fragments were used either alone or, preferably, together.

The transformed tissue [was] *is* selected for glyphosate resistance using the method described below. First, the beamed embryogenic callus [was] *is* maintained for one month on B1-30 3Co5My0.01PA medium. Table 1 shows the composition of B1-30 3Co5My0.01PA medium.

TABLE 1

Ingredients in 1 liter B1-30 3Co5My0.10PA Medium (pH 5.8)

| | |
|---|---|
| MS Salts* | 4.43 g |
| NaEDTA | 37.3 mg |
| 2,4 dichlorophenoxyacetic acid | 30 mg |
| Phytagar | 8 g |
| Coconut water | 30 ml |
| Myo-inositol | 5 g |
| Phytic acid | 10 mg |

*Sigma Plant Culture catalogue, reference M5519

The tissue [was] *is* then transferred to the same medium but now containing 300 mg/l glyphosate. After a number of passages (up to 5 passages, each passage may last for about a month) on this latter medium, resistant clonal material may be identified. After an optional further few passages on B1-30 3Co5My0.01PA medium but containing 500 mg/l glyphosate, the growing tissue [was] *is* transferred to a regeneration media as described in U.S. patent Ser. No. 09/450,226. Regenerated plants [were] *are* transferred to pots in a greenhouse. These plants and their progenies [were] *are* sprayed with glyphosate at commercial rates, and complete resistance to glyphosate [was] *is expected to be* observed. Progenies [segregated] *are expected to segregate* 3:1 for glyphosate resistance as would be expected for Mendelian inheritance of a transgene.

Preferably, both mutant epm1 (such as SEQ ID NO: 2) and mutant epm2 (such as SEQ ID NO: 4) are stably transformed into a plant cell, from which glyphosate-resistant plants can be regenerated.

EXAMPLE 3

Preparation and Mutation of Corn Genomic Fragments Containing EPSPS Gene

A corn (B 73) BAC library was screened with a probe containing a sequence of a corn EPSPS gene published in Genbank accession number X63374 by Incyte Genomics Inc. Four BAC clones were identified. Southern blot analysis indicated that all four clones contained the same EPSPS gene. One BAC clone was further characterized by nucleotide sequencing which resulted in identification of a 6.0 kb genomic fragment flanked by unique Cla I and Eco RV sites. The sequence of the 6.0 kb fragment was shown as SEQ ID NO: 5. The 6.0 kb fragment includes an EPSPS 5' regulatory sequence (the sequence before nucleotide 1868), an EPSPS coding sequence (from nucleotide 1868 to nucleotide 5146), and an EPSPS 3, regulatory sequence (the sequence after nucleotide 5146). The EPSPS coding sequence also encodes a chloroplast transit peptide (from nucleotide 1868 to nucleotide 2041). The sequence encoding this chloroplast transit peptide can be predicted using the computer program PS ORT maintained on the public accessible GenomeNet at Kyoto University, Japan.

The 6.0 kb fragment was cloned into the Cla I and Eco RV sites of a pbluescript vector, and then subject to site directed mutagenesis using QuikChange Site-Directed Mutagenesis Kit (Stratagene). Two mutations were introduced into the EPSPS coding sequence: the first mutation being a cytosine to thymine substitution at nucleotide 2886 and the second mutation being a cytosine to thymine substitution at nucleotide 2897. The mutated sequence is shown as SEQ ID NO: 6. The mutations changed the encoded amino acid residue Thr to Ile at position 164 and Pro to Ser at position 168. This mutated EPSPS amino acid sequence is shown as SEQ ID NO: 9. The mutated EPSPS is glyphosate-resistant. The pBluescript vector comprising SEQ ID NO: 6 is referred to as HCEM.

EXAMPLE 4

Transformation of Corn

The Cla I and Eco RV fragment (SEQ ID NO: 6) of HCEM was introduced into cultured immature corn embryos using an aerosol beam injector according to U.S. patent application Ser. No. 09/450,226. The Cla I-Eco RV fragment comprised the glyphosate-resistant EPSPS coding sequence.

Selection was carried out as follows: the beamed embryos were allowed to remain on DN62A0S20G medium for 5 days. Table 2 shows the composition of DN62A0S20G medium.

TABLE 2

Ingredients in 1 liter Culture Medium (pH 5.8)

| | DN62A0S20G | DN62A0S20GLC |
|---|---|---|
| N6 Salts* | 3.98 g | 3.98 g |
| N6 Vitamins | 1 ml | 1 ml |
| Asparagine | 800 mg | 800 mg |
| Myoinositol | 100 g | 100 g |
| Proline | 1400 mg | 1400 mg |
| Casamino acids | 100 mg | 100 mg |
| 2,4 dichlorophenoxyacetic acid | 1 mg | 1 mg |
| Glucose | 20 g | 20 g |
| Silver nitrate | 10 mg | 10 mg |
| Cefotaxime | 0 mg | 50 mg |

*Sigma Plant Culture catalogue, reference C1416

The beamed embryos were then transferred to DN62A100RR a medium containing 100 mg/l glyphosate. Table 3 lists the composition of DN62A100RR and other media. After two 14-day passages on DN62A100RR, actively growing tissue [was] *is* transferred to DN62A300RR medium which contains 300 mg/l (Table 3). After two 14-day passages on this medium, tissue was finally transferred to DN62540RR medium which contains 540 mg/l glyphosate (Table 3). Stable transformation allowed continued growth on 540 mg/l glyphosate. Regeneration [was] *is* carried out as described in U.S. patent application Ser. No. 09/450,226.

TABLE 3

Ingredients in 1 liter Culture Medium (pH 5.8)

| | DN62A100R R | DN62ALC180R R | DN62A300R R | DN62540RR |
|---|---|---|---|---|
| N6 Salts* | 3.98 g | 3.98 g | 3.98 g | 3.98 g |
| N6 Vitamins | 1 ml | 1 ml | 1 ml | 1 ml |
| Asparagine | 800 mg | 800 mg | 800 mg | 800 mg |
| Myoinositol | 100 mg | 100 mg | 100 mg | 100 mg |
| Proline | 1400 mg | 1400 mg | 1400 mg | 1400 mg |
| Casamino acids | 100 mg | 100 mg | 100 mg | 100 mg |
| 2,4 dichlorophenoxyacetic acid | 1 mg | 1 mg | 1 mg | 1 mg |
| Sucrose | 20 g | 20 g | 20 g | 20 g |
| Silver nitrate | 10 mg | 10 mg | 10 mg | |
| Glyphosate | 100 mg | 180 mg | 300 mg | 540 mg |
| Cefotaxime | 0 mg | 50 mg | 0 mg | 0 mg |

*Sigma Plant Culture catalogue, reference C1416

Transformation can also be accomplished using Agrobacterium-mediated DNA delivery. In this case, the transformation and regeneration [were] *are* performed according to the methods as described in U.S. patent application Ser. No. 09/203,679, which is herein incorporated by reference. Briefly, after culturing on DN62A0S20GLC (Table 2) for five days, co-cultivated embryos [were] *are* transferred to DN62ALC180RR medium which contains 180 mg/l glyphosate (Table 3). After two 14-day passages on this medium, actively growing tissue [was] *is* transferred to DN62540RR medium containing 540 mg/l glyphosate (Table 3). Stable transformation [allowed] *will allow* continued growth on 540 mg/l glyphosate. Regeneration [was] *is* carried out as described in U.S. Ser. No. 09/203,679.

Resistance to glyphosate in regenerants [was] *is* confirmed by spraying them with glyphosate at commercial rates. Seed from the regenerants [segregated] *is expected to segregate* 3:1 for resistance as would be expected with Mendelian inheritance of a transgene. Seeds from backcrossed individuals [segregated] *are expected to segregate* 1:1. Corn transformation may also be accomplished by other means including, for example, particle bombardment or electroporation of competent cells.

SEQUENCE LISTING

<160> NUMBER OF SEQ ID NOS: 9

<210> SEQ ID NO 1
<211> LENGTH: 4706
<212> TYPE: DNA
<213> ORGANISM: Arabidopsis thaliana

<400> SEQUENCE: 1 ccgcggtggc ggcttggact caaccggaaa caaaagtgtc gaaagtagcc ggtgatgatg 60 aagaatcacg gcgcgttatg agaaaaatac agagctctgg gagattgtct cgctcctgtc 120 gtgttaccgc cacgtggccg gaggagaagc tccttatgaa tgtaggaagt tacgatagta 180 accttcccgt cggcgagttt gatcttgccg aggcgtggag actggtgatc gtgaccgtga 240 gcttggatgg gatgattagg acattccata actatggact gccacgtaca ttttagagat 300 cgataatcta tttttgtttt aaataggaga aaacaaaaat tgatttttg tttggttttt 360 gttttggtgt ctaaatatat gtagattttc tagtttctag tccttcgctt ccaagttcct 420 cgatggctca atgccaattt agtcagataa gattatgctg caactgctag agcgactctc 480 tcctacttca ttttagtcca tactagttca ttttatctcc aagaaaatga ctccgttttg 540 cttcaaagct caaagatgat tctttttta atgggccctc ttgaaaaatg ggtaaaatct 600 tggtcttttt acagatagca aacatataca aattatggag aaaacaggat tatattgatg 660 cagcttcgtt gtagacagac ttgtagtcgt tttcttcatt ttcccattcc tctgctaaat 720 tattaaatcc aacaaaaaca aattttcttc tgttgcttga taaaatctat gtggaatatc 780 tatatctaca cactactgaa gaccaagaag taaacattag tttgcctgat cttcacctac 840 ctcaaacgag aagtagaagt ttttatggtg acttttgtat ttagagaaac aatgggattc 900 cagtttaagt tggctctttt taactttgct aacatatgcc tgaaagtgga agacaagaac 960 ttggtttaag aaacctcaag cgattgcgat tttgggtctt aagcttgaaa aaagtgttgt 1020 atggaacaaa caaactaaca tatcggaaca agcttggctt tggttttaaa gctgatagat 1080 aatggtcgaa ccataaccgg tatggcccaa gatgttcatg ttttttaaaa ctcaccaaag 1140 ctatatcact aacccacaca ttcttgcaga aggttttaga atcacaaagc ataactcacc 1200 taccccctaaa ccaactccaa tttctctcct cctctattaa atctttctca atcatctttc 1260 tttgagtctt ttgccttgga atcctgatca tggcgtcttc tctcacttcc aaatccattc 1320 tcggatgcac caaacccgct tcttcttctt ttcttccgtc ggagctccgt cgtctctctt 1380 ctcccgccgt tcagatatct ctccattcac aaaccaggaa gaacttccgt gagttctctg 1440 attcttttca aaatttttag atttgaagcc tgtatctagc ttaaagaaga aagatgtgtg 1500 atttgaatct ctagggcagt cgtggggatt gaagaagagt gatctgatgc taaatggttc 1560 tgagattcgt cctgtgaagg ttagggcttc tgtttccacg gcggagaaag cttcggagat 1620 tgtgcttcaa cccattagag aaatctcggg tctcattaag cttcctggct ccaagtctct 1680 ctctaatcga attctgcttc tcgctgctct atctgaggta tatataaatg tatcacttca 1740 tttcttcctt ctctgtactc cgaatttaga ttattaaaga tataaacttt accattttgc 1800 tgtgcttata tagggaacta ctgtagtgga caacttgttg aacagtgatg acatcaatta 1860 catgcttgat gcgttgaaga tattgggact taatgtggaa actcacagtg aaaacaatcg 1920 tgctgtagtt gaaggatgtg gcggggtatt tccagcttcc attgattcca agagtgatat 1980 cgaactttac ctcggcaatg caggaacagc aatgcgtcca cttaccgccg cagttactgc 2040

-continued

```
tgcaggtggc aacgcaaggt atattgaagg agtaaatgct gaatagtttt gatttcttaa   2100
gaatcgatct tgttttgatg cttttcaatc ggtttatttc agttatgtcc ttgatggggt   2160
gcctcggatg agagagagac ctatagggga tttggttgtt ggtcttaagc agcttggtgc   2220
tgatgttgaa tgtactcttg gcactaactg ccctcctgtt cgtgtcaacg ctaatggtgg   2280
ccttcctggt ggaaaggtga gatcttgcaa atggcatgtg aatttataac tttataaaca   2340
cttgcagcaa tttgtgttca tcatagcctt acttgacaag atttcatttt ttttgtttgt   2400
tgtcaatgta ttgttcctga aaacgaattg tttttttta gtagggatta gttttctctc   2460
ttgattaccc ttttccttgt atggtttctt tattgacgca tcgaacattt tttgcatttg   2520
caggtgaagc tttctggatc tattagtagt cagtacttga ccgctctgct catggcagct   2580
cccttagctc ttggagacgt cgaaattgaa attgtcgata aattgatttc tgttccgtat   2640
gttgaaatga cattgaagtt gatggaacgt tttggggtaa gtgctgagca tagtgaaagc   2700
tgggatcgtt tctttgttaa gggtgggcaa aaatacaagt aagagttatt attctcttcc   2760
ttttctgaaa tcacatacct tagattgaca aaataatgac taatatggga aatgattcag   2820
gtcgccgggt aatgcttacg tagaaggtga tgcttctagt gctagttatt tcctggctgg   2880
tgctgccatt accggtgaaa ctgtcactgt tgaaggttgt ggaacgacca gtttgcaggt   2940
aatatttgta cactgaatca tcaaagaggc tgttaagttt atagtgaaat tcgtttaggt   3000
caaagtttca tctttttaag gctttgacaa gttgtatgta acatattcgc aagaatctaa   3060
gttcaatttt tgtgatgaat ctctagggag atgtgaaatt tgccgaggtt cttgagaaaa   3120
tgggatgtaa agtgtcctgg acagagaaca gtgtgactgt gacagggccg tctagagatg   3180
cttttggaat gagacacttg cgggctattg atgtcaacat gaacaaaatg cctgatgtag   3240
caatgactct tgccgtcgtt gctctctttg ccgatggtcc aaccaccatt agagatggta   3300
agtaaaaagc tctctcttat aatataaggt ttctcaagat tcatggtcac ttaattctat   3360
ttggtcaata tagtggctag ctggagagta aaggagacgg aaaggatgat tgccatttgc   3420
acagagctta gaaaagtaaa attcttcttc tctctctctc tttctgttta cagtgctcat   3480
tctaagaaat tttgcggtat ttgtgtccag ctgggagcta cagtggaaga aggttcagat   3540
tattgtgtga ttactccgcc gaaaaaggtg aaaccggcag agattgatac atatgatgat   3600
catagaatgg caatggcatt ctctcttgca gcttgtgctg atgttccaat caccatcaat   3660
gaccccggtt gcaccaggaa aaccttcccc gactacttcc aagtccttga aagaatcaca   3720
aagcattaaa caaaaaaact ctaaaatctc cactgttttt tcttctgatc caagcttatc   3780
tgtttccatt tttcttgtct ctgtaacatt attagaaagc aagagtagtg tttgtttgtg   3840
tgtacctgaa ctgagtgaga tttgagatgc aatcattgaa tcggctttgg tatatcattt   3900
tactctgttt ttcagggtgt ttgttcaggt tctctctagt tatcatccac tccaaacagg   3960
tcccatgatg tctaacgttt tggttctaag aatgaacaga acaaacaata cactgcgata   4020
accggtgctt ggaagttgtg ttaattgaag aaacaatggc aatagctgca tacttatagt   4080
tgcaggagtg aaaaatgaga taagaggaat gcaaatatgc aattgcaggt tctatttttt   4140
ttttgctgcc aatgttatta ccaaaagggc tacaagtgag tattctccaa gcttggatga   4200
ggttattcag ggtaataggg tatcaagtta gtaataagag tcagagatac catgaaagga   4260
ttccaagttg tagtaagaac aactcaaatt caaagtgaag ttttgtgagt tgtgtaattg   4320
tgttggagtt ttgcacaaat gagaagactc ttatagaaac agaggggttg aagaagaagc   4380
gatatttgcc catctcactt gaaaacacta accggagata aaccaaatta attggaacta   4440
```

-continued

```
ttctcagtta tggtttggtc ctcgtcgttt tgggttagtg ttgttggtag gtggagaatt   4500

ttgcatttgc atttgcacaa cgaagaagaa gaccacaaga gccatttgca attaggcata   4560

atatatgtcc taactcacca acccccctcaa aattgccacc aacttcaaat ttctctcctt   4620

taaacctttc tcaatcatct ttcttctgcc ttggaatcct gatcatggcg tcgtcttctc   4680

tcacttcgaa atccattctc ggatcc                                        4706


<210> SEQ ID NO 2
<211> LENGTH: 4706
<212> TYPE: DNA
<213> ORGANISM: Arabidopsis thaliana
<220> FEATURE:
<221> NAME/KEY: misc_feature
<222> LOCATION: (2007)..(2007)
<223> OTHER INFORMATION: substituting thymine for cytosine at position
      2007 as compared to SEQ ID NO: 1
<220> FEATURE:
<221> NAME/KEY: misc_feature
<222> LOCATION: (2018)..(2018)
<223> OTHER INFORMATION: substituting thymine for cytosine at position
      2018 as compared to SEQ ID NO: 1

<400> SEQUENCE: 2

ccgcggtggc ggcttggact caaccggaaa caaaagtgtc gaaagtagcc ggtgatgatg     60

aagaatcacg gcgcgttatg agaaaaatac agagctctgg gagattgtct cgctcctgtc    120

gtgttaccgc cacgtggccg gaggagaagc tccttatgaa tgtaggaagt tacgatagta    180

accttcccgt cggcgagttt gatcttgccg aggcgtggag actggtgatc gtgaccgtga    240

gcttggatgg gatgattagg acattccata actatggact gccacgtaca ttttagagat    300

cgataatcta tttttgtttt aaataggaga aaacaaaaat tgatttttg tttggttttt    360

gttttggtgt ctaaatatat gtagattttc tagtttctag tccttcgctt ccaagttcct    420

cgatggctca atgccaattt agtcagataa gattatgctg caactgctag agcgactctc    480

tcctacttca ttttagtcca tactagttca ttttatctcc aagaaaatga ctccgttttg    540

cttcaaagct caaagatgat tctttttta atgggccctc ttgaaaaatg ggtaaaatct    600

tggtcttttt acagatagca aacatataca aattatggag aaaacaggat tatattgatg    660

cagcttcgtt gtagacagac ttgtagtcgt tttcttcatt ttcccattcc tctgctaaat    720

tattaaatcc aacaaaaaca aattttcttc tgttgcttga taaaatctat gtggaatatc    780

tatatctaca cactactgaa gaccaagaag taaacattag tttgcctgat cttcacctac    840

ctcaaacgag aagtagaagt ttttatggtg acttttgtat ttagagaaac aatgggattc    900

cagtttaagt tggctctttt taactttgct aacatatgcc tgaaagtgga agacaagaac    960

ttggtttaag aaacctcaag cgattgcgat tttgggtctt aagcttgaaa aaagtgttgt   1020

atggaacaaa caaactaaca tatcggaaca agcttggctt tggttttaaa gctgatagat   1080

aatggtcgaa ccataaccgg tatggcccaa gatgttcatg ttttttaaaa ctcaccaaag   1140

ctatatcact aacccacaca ttcttgcaga aggttttaga atcacaaagc ataactcacc   1200

taccccctaaa ccaactccaa tttctctcct cctctattaa atctttctca atcatctttc   1260

tttgagtctt ttgccttgga atcctgatca tggcgtcttc tctcacttcc aaatccattc   1320

tcggatgcac caaacccgct tcttcttctt ttcttccgtc ggagctccgt cgtctctctt   1380

ctcccgccgt tcagatatct ctccattcac aaaccaggaa gaacttccgt gagttctctg   1440

attcttttca aaatttttag atttgaagcc tgtatctagc ttaaagaaga aagatgtgtg   1500

atttgaatct ctagggcagt cgtggggatt gaagaagagt gatctgatgc taaatggttc   1560
```

-continued

```
tgagattcgt cctgtgaagg ttagggcttc tgtttccacg gcggagaaag cttcggagat   1620
tgtgcttcaa cccattagag aaatctcggg tctcattaag cttcctggct ccaagtctct   1680
ctctaatcga attctgcttc tcgctgctct atctgaggta tatataaatg tatcacttca   1740
tttcttcctt ctctgtactc cgaatttaga ttattaaaga tataaacttt accattttgc   1800
tgtgcttata tagggaacta ctgtagtgga caacttgttg aacagtgatg acatcaatta   1860
catgcttgat gcgttgaaga tattgggact taatgtggaa actcacagtg aaaacaatcg   1920
tgctgtagtt gaaggatgtg gcggggtatt tccagcttcc attgattcca agagtgatat   1980
cgaactttac ctcggcaatg caggaatagc aatgcgttca cttaccgccg cagttactgc   2040
tgcaggtggc aacgcaaggt atattgaagg agtaaatgct gaatagtttt gatttcttaa   2100
gaatcgatct tgttttgatg cttttcaatc ggtttatttc agttatgtcc ttgatggggt   2160
gcctcggatg agagagagac ctatagggga tttggttgtt ggtcttaagc agcttggtgc   2220
tgatgttgaa tgtactcttg gcactaactg ccctcctgtt cgtgtcaacg ctaatggtgg   2280
ccttcctggt ggaaaggtga gatcttgcaa atggcatgtg aatttataac tttataaaca   2340
cttgcagcaa tttgtgttca tcatagcctt acttgacaag atttcatttt ttttgtttgt   2400
tgtcaatgta ttgttcctga aaacgaattg tttttttta gtagggatta gttttctctc   2460
ttgattaccc ttttccttgt atggtttctt tattgacgca tcgaacattt tttgcatttg   2520
caggtgaagc tttctggatc tattagtagt cagtacttga ccgctctgct catggcagct   2580
cccttagctc ttggagacgt cgaaattgaa attgtcgata aattgatttc tgttccgtat   2640
gttgaaatga cattgaagtt gatggaacgt tttggggtaa gtgctgagca tagtgaaagc   2700
tgggatcgtt tctttgttaa gggtgggcaa aaatacaagt aagagttatt attctcttcc   2760
ttttctgaaa tcacatacct tagattgaca aaataatgac taatatggga aatgattcag   2820
gtcgccgggt aatgcttacg tagaaggtga tgcttctagt gctagttatt tcctggctgg   2880
tgctgccatt accggtgaaa ctgtcactgt tgaaggttgt ggaacgacca gtttgcaggt   2940
aatatttgta cactgaatca tcaaagaggc tgttaagttt atagtgaaat tcgtttaggt   3000
caaagtttca tctttttaag gctttgacaa gttgtatgta acatattcgc aagaatctaa   3060
gttcaatttt tgtgatgaat ctctagggag atgtgaaatt tgccgaggtt cttgagaaaa   3120
tgggatgtaa agtgtcctgg acagagaaca gtgtgactgt gacagggccg tctagagatg   3180
cttttggaat gagacacttg cgggctattg atgtcaacat gaacaaaatg cctgatgtag   3240
caatgactct tgccgtcgtt gctctctttg ccgatggtcc aaccaccatt agagatggta   3300
agtaaaaagc tctctcttat aatataaggt ttctcaagat tcatggtcac ttaattctat   3360
ttggtcaata tagtggctag ctggagagta aaggagacgg aaaggatgat tgccatttgc   3420
acagagctta gaaaagtaaa attcttcttc tctctctctc tttctgttta cagtgctcat   3480
tctaagaaat tttgcggtat ttgtgtccag ctgggagcta cagtggaaga aggttcagat   3540
tattgtgtga ttactccgcc gaaaaaggtg aaaccggcag agattgatac atatgatgat   3600
catagaatgg caatggcatt ctctcttgca gcttgtgctg atgttccaat caccatcaat   3660
gaccccggtt gcaccaggaa aaccttcccc gactacttcc aagtccttga aagaatcaca   3720
aagcattaaa caaaaaaact ctaaaatctc cactgttttt tcttctgatc caagcttatc   3780
tgtttccatt tttcttgtct ctgtaacatt attagaaagc aagagtagtg tttgtttgtg   3840
tgtacctgaa ctgagtgaga tttgagatgc aatcattgaa tcggctttgg tatatcattt   3900
tactctgttt ttcagggtgt ttgttcaggt tctctctagt tatcatccac tccaaacagg   3960
```

-continued

```
tcccatgatg tctaacgttt tggttctaag aatgaacaga acaaacaata cactgcgata   4020

accggtgctt ggaagttgtg ttaattgaag aaacaatggc aatagctgca tacttatagt   4080

tgcaggagtg aaaaatgaga taagaggaat gcaaatatgc aattgcaggt tctatttttt   4140

ttttgctgcc aatgttatta ccaaaagggc tacaagtgag tattctccaa gcttggatga   4200

ggttattcag ggtaataggg tatcaagtta gtaataagag tcagagatac catgaaagga   4260

ttccaagttg tagtaagaac aactcaaatt caaagtgaag ttttgtgagt tgtgtaattg   4320

tgttggagtt ttgcacaaat gagaagactc ttatagaaac agaggggttg aagaagaagc   4380

gatatttgcc catctcactt gaaaacacta accggagata aaccaaatta attggaacta   4440

ttctcagtta tggtttggtc ctcgtcgttt tgggttagtg ttgttggtag gtggagaatt   4500

ttgcatttgc atttgcacaa cgaagaagaa gaccacaaga gccatttgca attaggcata   4560

atatatgtcc taactcacca acccccctcaa aattgccacc aacttcaaat ttctctcctt   4620

taaacctttc tcaatcatct ttcttctgcc ttggaatcct gatcatggcg tcgtcttctc   4680

tcacttcgaa atccattctc ggatcc                                        4706
```

<210> SEQ ID NO 3
<211> LENGTH: 5193
<212> TYPE: DNA
<213> ORGANISM: Arabidopsis thaliana

<400> SEQUENCE: 3

```
ctgtctagaa tctttccatt tttgcttaca aatatggcac aaccggaaat tcccttactt     60

atttatggaa aaacaaaagt gtcatgtgtt atatatattg gtccctttt atgtttgtag    120

ggctatcact accaatccac aatggaagat tcacaaccgt gtacatcacg taacctagat    180

catgccgaaa actccacagc aagcattcct cttaaactca tcttcgaaat actatcgagg    240

ctttcgacga aatttatcat cagattccga tccgtgtcga tgctgtgacg ctctatcatc    300

gatagtaaag atttcgtcga cgcctttctg aatcctcttt tttcaatgaa gactcttttt    360

ttagtccgct ttatggaata atacttatgt tttaacgtaa tgaatcttta tatctatttg    420

tatttttcag ttacactttt gtttggacgt tttgttttca aagaacttct caagttttct    480

tttccttttt tcttcttgta gtttgccttg ctcgttggtg aatacactac attaattgag    540

ggcacttgcg attatgatgt tctcccgcgt gaaagagcat tgacctctct tttattcaaa    600

acatcacata acagagagtc tgtgaggttt gggacatcgc attctcaaat ctcaatataa    660

gtggttttgg tcgaatgcta gaaaagggtg acttgtatgt tgtgtcgccg ctagtgttcg    720

tacatacagt ttatgatcta acgtatctat aacatattat taatagatat tattttgttt    780

taattttgca cattgtttat aaattaagtg caaaaatttt tagctccaag agatcgcctt    840

tgctaatcaa taaaattgaa cgcatttaat aaaattgtaa gagcaaactc gcactgatac    900

gtagaataaa tttgttgctt ttgccttcac gacaccatta cctatagtta atactccaaa    960

agaaatagca gattcaacat acaacgtgca agaccaaaaa acaaatgact cgtaatctcc   1020

agagaatcat aattcataac atgggagatt gtccacaaaa aacataaatt ccctttcatg   1080

tctttttgtt agaaaaccca tttcttaagg cccaacaaaa aacataatcc cctttcatgt   1140

ctttttgtta gaaaccccat ttatctttct tgaggcccaa tttgaaaacc cacattttct   1200

ttcacctaac ccaccaaagc ctttgcacat gttgacgtga acaccaaact aacacgtgtc   1260

atactgccag tggttatgat aaatgctcat accataccag agtcatagag tttttggttg   1320

gtgaaagatt tgacggatgc cttcttctca tttctcacca actccctcca aacccaacaa   1380
```

-continued

```
aagtgtttat attagcaaag ccgccaaagt gtaaacgaaa gtttataaat ttcatttctg   1440
tgatcttacg taattggagg aagatcaaaa ttttcaatcc ccattcttcg attgcttcaa   1500
ttgaagtttc tccgatggcg caagttagca gaatctgcaa tggtgtgcag aacccatctc   1560
ttatctccaa tctctcgaaa tccagtcaac gcaaatctcc cttatcggtt tctctgaaga   1620
cgcagcagca tccacgagct tatccgattt cgtcgtcgtg gggattgaag aagagtggga   1680
tgacgttaat tggctctgag cttcgtcctc ttaaggtcat gtcttctgtt tccacggcgg   1740
agaaagcgtc ggagattgta cttcaaccca ttagagaaat ctccggtctt attaagcttc   1800
ctggctccaa gtctctatca aatcggatcc tgcttctcgc tgctctgtct gaggtatata   1860
tcacttcgtt tcgtccttct ctgtaatctg aacttagatt ataaagattg atactttacc   1920
attttgctgt ggttttatag ggaacaactg tagtggacaa cttgttgaat agcgatgaca   1980
tcaattacat gcttgatgcg ttgaagagat tgggacttaa tgtggaaact gacagtgaaa   2040
ataatcgtgc tgtagttgaa ggatgtggcg ggatattccc agcttccata gattcaaaga   2100
gtgatatcga actttacctc ggtaatgcag gaacagcaat gcgtccactt accgctgcgg   2160
tcactgctgc aggtggaaac gcaaggtaga ttgaaggagt tgatgcttct tggtatttga   2220
tgtttaagga atggagcttt tgttgatgct ttatgatcca tttattccag ttatgtgctt   2280
gatggggtgc ctcgtatgag agaaagacct ataggggatt tggttgttgg tcttaagcag   2340
cttggtgctg atgttgaatg tactcttgga actaactgcc ctcctgttcg tgtcaacgct   2400
aatggtggcc ttcccggtgg aaaggttaga tcttgcaaat ggcatgtgaa tatgtaatct   2460
cgttccttac tctatgaaca cttgcagaaa tgtgtgttca tcatagcctt agcttgacaa   2520
gatttcagtt tttaatctac tctcaacgga tggatcctaa aatagaatcg gatttggtga   2580
ttggttttcg ttctcgatta ccgttttcgt tgtatgattt cttgattaac aattaggaga   2640
catgttatgc atttgcaggt gaagctttct ggatcaatta gtagtcagta cttgactgct   2700
ctgctcatgt ctgctccctt agctcttgga gacgtcgaga ttgagattgt cgataaatta   2760
atttctgttc catatgttga aatgacattg aagttgatgg aacgtttcgg ggttagtgtc   2820
gagcatagtg atagctggga tcgtttcttt gtcaagggcg ggcaaaaata caagtaggag   2880
ttattctttt cttccttttc tgaaatcaca tcccttagct tgacaatata atgactaaaa   2940
ggtgaatgat tcaggtctcc gggtaatgcg tatgtagaag gtgatgcttc tagtgctagt   3000
tatttcttgg ctggtgctgc cattaccggt gaaactgtca cagtcgaagg ttgtggaact   3060
accagcttgc aggtaatatt tgtacactga atcatcgacg aggctgttaa gtttatagtg   3120
aaattcgtct aggtcaaagt ttcatctttt gacaagttgt atataacata ttcgcaagaa   3180
tctaagctca atttttgtga tgaatctcta gggagatgta aaattcgccg aggtccttga   3240
gaaaatggga tgtaaagtgt cctggacaga gaacagtgtg actgtgacag gaccacctag   3300
agatgctttt ggaatgagac acttgcgggc tattgatgtc aacatgaaca aaatgcctga   3360
tgtagccatg acccttgccg tcgttgctct ctttgctgac ggtccaacca ccattagaga   3420
tggtaagtaa aaagctctct cttataatta aggtttctca atattcatga tcacttaatt   3480
ctgtttggtt aatatagtgg ctagctggag agtaaaggag acagaaagga tgattgccat   3540
ttgcacagag cttagaaaag taagagattc ttatctctct ctttctgtct cttgacagtg   3600
ctcattctaa gtaattagct cataaatttt gtgtgtttgt gttcagctgg gagctacagt   3660
ggaagaaggt tcagattatt gtgtgataac tccgcccaaa aaggtgaaaa cggcagagat   3720
tgatacatat gatgatcata gaatggcaat ggcattctct cttgcagctt gtgctgatgt   3780
```

-continued

```
tccaatcacc atcaacgatc ctggttgcac caggaaaacc ttccccgact acttccaagt   3840

acttgaaaga atcacaaagc actaaacaat aaactctgtt ttttcttctg atccaagctt   3900

atctgtttcc atttttcttg tctctgtaat attattagaa accgagagtg tttgtttgcg   3960

tgtaactgaa ctgagcgagt tttgagatgc aatcatttga gttcgattga gagaaatgaa   4020

tgtgtagaga tttcctttta tcttgatgga aagaaattga gttttccttc ttctcttttt   4080

tttccaattc ctaggtcgtc gactcgaata tataaagaca gcagccacga tcgtctcttt   4140

tgatcactta ttagagacaa taatgttgga aagacatggt tcctctagtt tggtattgaa   4200

aagacatcgt tcttgtttgg aattgctgcc acacgatgta gtagagctca tcctcgagag   4260

acacagttga tcggtcacga gaacaatatt atagatgaag ctcaaaggag gagaatagtg   4320

ttgttggggt cgtcatcgta attagcaaac taactgtgag ttcccgtcaa agaccattta   4380

tggcccacgt aaaacgacgc cgtttaaatc tgagtcaaag cccatttgtg gcccacgtcc   4440

taacacagtc gtttctctcc gactagtaaa ctaaaatccc ggaaattctc atccgcatga   4500

gctccggtga aaaatggaga ccaagagaaa gtaagcagga gcctctcgtc tctgcaatct   4560

gagacatcga aagaccgaaa atccttcaac aggtaacatt tcaatttcgc cttcgcctag   4620

aaagaagctc gtgtttgttt ttgggtttta gctaagaatt ttagggaaaa gcttgaaaca   4680

aatttggctc tcttatcaat tgcatttgtt ttggagttat gattctgtgt ggaatcgaat   4740

caaaattatc aatctgaaag tgacaataat cccttgtttg tcttttgtgt tttttatttg   4800

agttcggttt acatggtttc gaacttttca attgattttt gggtttcggt ttgcattgga   4860

attaataagg ttttgagaag agaaaagaaa aaaaggcacg cacgcgaggc gtttttagag   4920

aggggcgagt gtggttcaaa ataggcgttt tggtgggtta gaacccacag aaattggatt   4980

cacgcgccaa acgcaagatg ggcgagagtg ggtatgaaat ggtaagatcg gtgagaatgg   5040

ggtatgacat ggagggctct gattggctaa taaactcaaa atagtagaca tatagctcct   5100

cccttcctcc tctcataata atagtagtta ttattactta gtcttatatg cgaagaaaca   5160

atgaatgaaa aaaccttact tgggtcggaa ttc                                5193
```

```
<210> SEQ ID NO 4
<211> LENGTH: 5193
<212> TYPE: DNA
<213> ORGANISM: Arabidopsis thaliana
<220> FEATURE:
<221> NAME/KEY: misc_feature
<222> LOCATION: (2134)..(2134)
<223> OTHER INFORMATION: substituting thymine for cytosine at position
      2134 as compared to SEQ ID NO: 3
<220> FEATURE:
<221> NAME/KEY: misc_feature
<222> LOCATION: (2145)..(2145)
<223> OTHER INFORMATION: substituting thymine for cytosine at position
      2145 as compared to SEQ ID NO: 3

<400> SEQUENCE: 4

ctgtctagaa tctttccatt tttgcttaca aatatggcac aaccggaaat tcccttactt     60

atttatggaa aaacaaaagt gtcatgtgtt atatatattg gtccctttt atgtttgtag    120

ggctatcact accaatccac aatggaagat tcacaaccgt gtacatcacg taacctagat    180

catgccgaaa actccacagc aagcattcct cttaaactca tcttcgaaat actatcgagg    240

ctttcgacga aatttatcat cagattccga tccgtgtcga tgctgtgacg ctctatcatc    300

gatagtaaag atttcgtcga cgcctttctg aatcctcttt tttcaatgaa gactcttttt    360

ttagtccgct ttatggaata atacttatgt tttaacgtaa tgaatcttta tatctatttg    420
```

-continued

```
tatttttcag ttacactttt gtttggacgt tttgttttca aagaacttct caagttttct    480
tttccttttt tcttcttgta gtttgccttg ctcgttggtg aatacactac attaattgag    540
ggcacttgcg attatgatgt tctcccgcgt gaaagagcat tgacctctct tttattcaaa    600
acatcacata acagagagtc tgtgaggttt gggacatcgc attctcaaat ctcaatataa    660
gtggttttgg tcgaatgcta gaaaagggtg acttgtatgt tgtgtcgccg ctagtgttcg    720
tacatacagt ttatgatcta acgtatctat aacatattat taatagatat tattttgttt    780
taattttgca cattgtttat aaattaagtg caaaaatttt tagctccaag agatcgcctt    840
tgctaatcaa taaaattgaa cgcatttaat aaaattgtaa gagcaaactc gcactgatac    900
gtagaataaa tttgttgctt ttgccttcac gacaccatta cctatagtta atactccaaa    960
agaaatagca gattcaacat acaacgtgca agaccaaaaa acaaatgact cgtaatctcc   1020
agagaatcat aattcataac atgggagatt gtccacaaaa aacataaatt ccctttcatg   1080
tctttttgtt agaaaaccca tttcttaagg cccaacaaaa aacataatcc cctttcatgt   1140
ctttttgtta gaaaccccat ttatctttct tgaggcccaa tttgaaaacc cacattttct   1200
ttcacctaac ccaccaaagc ctttgcacat gttgacgtga acaccaaact aacacgtgtc   1260
atactgccag tggttatgat aaatgctcat accataccag agtcatagag tttttggttg   1320
gtgaaagatt tgacggatgc cttcttctca tttctcacca actccctcca aacccaacaa   1380
aagtgtttat attagcaaag ccgccaaagt gtaaacgaaa gtttataaat ttcatttctg   1440
tgatcttacg taattggagg aagatcaaaa ttttcaatcc ccattcttcg attgcttcaa   1500
ttgaagtttc tccgatggcg caagttagca gaatctgcaa tggtgtgcag aacccatctc   1560
ttatctccaa tctctcgaaa tccagtcaac gcaaatctcc cttatcggtt tctctgaaga   1620
cgcagcagca tccacgagct tatccgattt cgtcgtcgtg gggattgaag aagagtggga   1680
tgacgttaat tggctctgag cttcgtcctc ttaaggtcat gtcttctgtt tccacggcgg   1740
agaaagcgtc ggagattgta cttcaaccca ttagagaaat ctccggtctt attaagcttc   1800
ctggctccaa gtctctatca aatcggatcc tgcttctcgc tgctctgtct gaggtatata   1860
tcacttcgtt tcgtccttct ctgtaatctg aacttagatt ataaagattg atactttacc   1920
attttgctgt ggttttatag ggaacaactg tagtggacaa cttgttgaat agcgatgaca   1980
tcaattacat gcttgatgcg ttgaagagat tgggacttaa tgtggaaact gacagtgaaa   2040
ataatcgtgc tgtagttgaa ggatgtggcg ggatattccc agcttccata gattcaaaga   2100
gtgatatcga actttacctc ggtaatgcag gaatagcaat gcgttcactt accgctgcgg   2160
tcactgctgc aggtggaaac gcaaggtaga ttgaaggagt tgatgcttct tggtatttga   2220
tgtttaagga atggagcttt tgttgatgct ttatgatcca tttattccag ttatgtgctt   2280
gatggggtgc ctcgtatgag agaaagacct ataggggatt tggttgttgg tcttaagcag   2340
cttggtgctg atgttgaatg tactcttgga actaactgcc ctcctgttcg tgtcaacgct   2400
aatggtggcc ttcccggtgg aaaggttaga tcttgcaaat ggcatgtgaa tatgtaatct   2460
cgttccttac tctatgaaca cttgcagaaa tgtgtgttca tcatagcctt agcttgacaa   2520
gatttcagtt tttaatctac tctcaacgga tggatcctaa aatagaatcg gatttggtga   2580
ttggttttcg ttctcgatta ccgttttcgt tgtatgattt cttgattaac aattaggaga   2640
catgttatgc atttgcaggt gaagctttct ggatcaatta gtagtcagta cttgactgct   2700
ctgctcatgt ctgctccctt agctcttgga gacgtcgaga ttgagattgt cgataaatta   2760
atttctgttc catatgttga aatgacattg aagttgatgg aacgtttcgg ggttagtgtc   2820
```

-continued

```
gagcatagtg atagctggga tcgtttcttt gtcaagggcg ggcaaaaata caagtaggag   2880
ttattctttt cttccttttc tgaaatcaca tcccttagct tgacaatata atgactaaaa   2940
ggtgaatgat tcaggtctcc gggtaatgcg tatgtagaag gtgatgcttc tagtgctagt   3000
tatttcttgg ctggtgctgc cattaccggt gaaactgtca cagtcgaagg ttgtggaact   3060
accagcttgc aggtaatatt tgtacactga atcatcgacg aggctgttaa gtttatagtg   3120
aaattcgtct aggtcaaagt ttcatctttt gacaagttgt atataacata ttcgcaagaa   3180
tctaagctca atttttgtga tgaatctcta gggagatgta aaattcgccg aggtccttga   3240
gaaaatggga tgtaaagtgt cctggacaga gaacagtgtg actgtgacag gaccacctag   3300
agatgctttt ggaatgagac acttgcgggc tattgatgtc aacatgaaca aaatgcctga   3360
tgtagccatg acccttgccg tcgttgctct ctttgctgac ggtccaacca ccattagaga   3420
tggtaagtaa aaagctctct cttataatta aggtttctca atattcatga tcacttaatt   3480
ctgtttggtt aatatagtgg ctagctggag agtaaaggag acagaaagga tgattgccat   3540
ttgcacagag cttagaaaag taagagattc ttatctctct ctttctgtct cttgacagtg   3600
ctcattctaa gtaattagct cataaatttt gtgtgtttgt gttcagctgg gagctacagt   3660
ggaagaaggt tcagattatt gtgtgataac tccgcccaaa aaggtgaaaa cggcagagat   3720
tgatacatat gatgatcata gaatggcaat ggcattctct cttgcagctt gtgctgatgt   3780
tccaatcacc atcaacgatc ctggttgcac caggaaaacc ttccccgact acttccaagt   3840
acttgaaaga atcacaaagc actaaacaat aaactctgtt ttttcttctg atccaagctt   3900
atctgtttcc atttttcttg tctctgtaat attattagaa accgagagtg tttgtttgcg   3960
tgtaactgaa ctgagcgagt tttgagatgc aatcatttga gttcgattga gagaaatgaa   4020
tgtgtagaga tttcctttta tcttgatgga aagaaattga gttttccttc ttctcttttt   4080
tttccaattc ctaggtcgtc gactcgaata tataaagaca gcagccacga tcgtctcttt   4140
tgatcactta ttagagacaa taatgttgga aagacatggt tcctctagtt tggtattgaa   4200
aagacatcgt tcttgtttgg aattgctgcc acacgatgta gtagagctca tcctcgagag   4260
acacagttga tcggtcacga gaacaatatt atagatgaag ctcaaaggag gagaatagtg   4320
ttgttggggt cgtcatcgta attagcaaac taactgtgag ttcccgtcaa agaccattta   4380
tggcccacgt aaaacgacgc cgtttaaatc tgagtcaaag cccatttgtg gcccacgtcc   4440
taacacagtc gtttctctcc gactagtaaa ctaaaatccc ggaaattctc atccgcatga   4500
gctccggtga aaaatggaga ccaagagaaa gtaagcagga gcctctcgtc tctgcaatct   4560
gagacatcga aagaccgaaa atccttcaac aggtaacatt tcaatttcgc cttcgcctag   4620
aaagaagctc gtgtttgttt ttgggtttta gctaagaatt ttagggaaaa gcttgaaaca   4680
aatttggctc tcttatcaat tgcatttgtt ttggagttat gattctgtgt ggaatcgaat   4740
caaaattatc aatctgaaag tgacaataat cccttgtttg tcttttgtgt tttttatttg   4800
agttcggttt acatggtttc gaacttttca attgattttt gggtttcggt ttgcattgga   4860
attaataagg ttttgagaag agaaaagaaa aaaaggcacg cacgcgaggc gtttttagag   4920
aggggcgagt gtggttcaaa ataggcgttt tggtgggtta gaacccacag aaattggatt   4980
cacgcgccaa acgcaagatg ggcgagagtg ggtatgaaat ggtaagatcg gtgagaatgg   5040
ggtatgacat ggagggctct gattggctaa taaactcaaa atagtagaca tatagctcct   5100
cccttcctcc tctcataata atagtagtta ttattactta gtcttatatg cgaagaaaca   5160
atgaatgaaa aaaccttact tgggtcggaa ttc                                5193
```

-continued

<210> SEQ ID NO 5
<211> LENGTH: 6010
<212> TYPE: DNA
<213> ORGANISM: Zea mays

<400> SEQUENCE: 5 atcgattgca accttcaaat tctcttcgat cttccttcca aattcatcta atatttcatc 60 ctcggcaagg aaatcttcta acgtgtaaac ttcactggga tccaactcga aaggatcaaa 120 ctctccctct ggttcgtttg acattgtgga tggagtgact aacctgctaa caccctgcaa 180 caatttatac aggagcatat cctcatgcac acgcaaaact gatgttgtcc acaagacacg 240 cacaggacac gcacaggaca cgcaaacagt ttcagactca tgcacacgca catcagtttc 300 agactcaggc acacgcacat caaatcacct tcgcttgtcg atgagtcgca gccgcatcgt 360 acaatggcga ttttaccgac gataaggcat gggagcacga gccgtcgccg tcgccttgcg 420 agacgacggg agcgatctct cccttcattt aatctcttcc acgtcaggtt attttgctga 480 gatggcagta tacagacggc aaagttaatg ccgttgtaca tgcccttaga ctcttccgtc 540 accaactcac ttagattttt acaacggaac ataaggttcg cttgcagact tacatataag 600 gtatagttgc ataataatcg ccttatgctg tacattgcga cacccgtaaa tattcgatga 660 aatattagta cacaatatta aataagaacg aacaatacat atattatcat tgatcttagt 720 atctcctttt gctcctcgta gaacaattct gtgtaaatta tgcgtaaaat tcgaggacca 780 aaacattggc tagaaaaata cctaaaatca gttttgcaat tgtttctgat tttcctcata 840 ttttcttgct tataaagttt tccaaaagta ccattttgga tgaaaaaacg gaaaacaacg 900 ctggtctact tgtaaatttg gtagtgacat ttgggaccgt ctagacacga cctaaaaata 960 gtagtctaaa acatagtctg acacgatgcc ttaaaaatag acgacaaagc acaacacgat 1020 tagatgtgtc gtgttttgac cgacacgaca caaagtaagg cacgatttaa aacccaataa 1080 ataatatttt aatggttatt ttatgttcca ataattttca tctcttcaaa aaaatgttat 1140 agaaatcatt gatacttagt tgaatatcct aacacaatat atatatatat attaatatat 1200 atatatatca attttaagtc actttgctag acatagtaat atattttaaa tattttctct 1260 ttcttgtata tttttaaaat acacatcagt ttttatatgt gtcgtgcttg aaccgacacg 1320 atataatcat cggttcgccg tacttctaga tcatgatgtt cctaggtttt aatattaaga 1380 gacggtctat attaactcaa aactatttcg tgaaaggcta actcgaaaaa aaaatgaatg 1440 taatcacggc ccgtcctgga ttcgagattc taacgtttca ttcgtgtcca gtgtgcacac 1500 ttgtggaaaa ggaagacgaa gaaaaaaacc aacaactaac tccggcccgc cggatgcgcc 1560 cacctacttc cccctcgccc ctctcatggt ctctctcgcg cccagatctg ctactagacg 1620 gcaccgctgc agcgcgtcgt gtcgcggggg ttggtggcag gcagcgagag cttgccgttc 1680 ctctctctca gttgtcaggt cctaggctca cctcaccggc tcccagcccg cttctatttc 1740 ttcctccccg accccgtgca ggtggcagtc cagtccacgc caccaaccgc gaggcgaacc 1800 aaaccaaccc actctcccca accccgcgcg cccaggccgc ccgccctacc aaccatcggc 1860 gtcggcaatg gcggccatgg cgaccaaggc cgccgcgggc accgtgtcgc tggacctcgc 1920 cgcgccgtcg cgccgccacc accgcccgag ctcggcgcgc ccgcccgccc gccccgccgt 1980 ccgcgggctg cgggcgcctg ggcgccgcgt gatcgccgcg ccgccggcgg cggcagcggc 2040 ggcggcggtg caggcgggtg ccgaggagat cgtgctgcag cccatcaagg agatctccgg 2100 caccgtcaag ctgccggggt ccaagtcgct ttccaaccgg atcctcctgc tcgccgccct 2160

-continued

```
gtccgaggtg agcgattttg gtgcttgctg cgctgccctg tctcactgct acctaaatgt   2220
tttgcctgtc gaataccatg gattctcggt gtaatccatc tcacgatcag atgcaccgca   2280
tgtcgcatgc ctagctctct ctaatttgtc tagtagtttg tatacggatt aatattgata   2340
aatcggtacc gcaaaagcta ggtgtaaata aacactagaa aattggatgt tcccctatcg   2400
gcctgtactc ggctactcgt tcttgtgatg gcatgctgtc tcttcttggt gtttggtgaa   2460
caaccttatg aaatttgggc gcaaagaact cgccctcaag ggttgatctt atgccatcgt   2520
catgataaac agtggagcac ggacgatcct ttacgttgtt tttaacaaac tttgtcagaa   2580
aactagcatc attaacttct taatgacgat ttcacaacaa aaaaaggtaa cctcgctact   2640
aacataacaa aatacttgtt gcttattaat tatatgtttt ttaatctttg atcaggggac   2700
aacagtggtt gataacctgt tgaacagtga ggatgtccac tacatgctcg gggccttgag   2760
gactcttggt ctctctgtcg aagcggacaa agctgccaaa agagctgtag ttgttggctg   2820
tggtggaaag ttcccagttg aggattctaa agaggaagtg cagctcttct tggggaatgc   2880
tggaactgca atgcggccat tgacagcagc tgttactgct gctggtggaa atgcaacgta   2940
tgtttcctct ctttctctct acaatacttg ctggagttag tatgaaaccc atgggtatgt   3000
ctagtggctt atggtgtatt ggtttttgaa cttcagttac gtgcttgatg gagtaccaag   3060
aatgagggag agacccattg gcgacttggt tgtcggattg aagcagcttg gtgcagatgt   3120
tgattgtttc cttggcactg actgcccacc tgttcgtgtc aatggaatcg gagggctacc   3180
tggtggcaag gttagctact aagggccaca tgttacattc ttctgtaaat ggtacaacta   3240
ttgtcgagct tttgcatttg taaggaaagc attgattgat ctgaatttga tgctacacca   3300
caaaatatcc tacaaatggt catccctaac tagcaaacaa tgaagtaata cttggcatgt   3360
gtttatcaaa ttaatttcca tcttctgggg cattgcctgt tttctagtct aatagcattt   3420
gtttttagca ttaattagct cttacaattg ttatgttcta caggtcaagc tgtctggctc   3480
catcagcagt cagtacttga gtgccttgct gatggctgct cctttggctc ttggggatgt   3540
ggagattgaa atcattgata aattaatctc cattccctac gtcgaaatga cattgagatt   3600
gatggagcgt tttggtgtga aagcagagca ttctgatagc tgggacagat tctacattaa   3660
gggaggtcaa aaatacaagt aagctctgta atgtatttca ctactttgat gccaatgttt   3720
cagttttcag ttttccaaac agtcgcatca atatttgaat agatgcactg tagaaaaaaa   3780
atcattgcag ggaaaaacta gtactgagta ttttgactgt aaattatttt accagtcgga   3840
atatagtcag tctattggag tcaagagcgt gaaccgaaat agccagttaa ttatcccatt   3900
atacagagga caaccatgta tactattgaa acttggttta taagagaatc taggtagctg   3960
gactcgtagc tgcttggcat ggataccttc ttatctttag gaaaagacac ttgatttttt   4020
ttttctgtgg ccctctatga tgtgtgaacc tgcttctcta ttgctttaga aggatatatc   4080
tatgtcgtta tgcaacatgc ttcccttagc catttgtact gaaatcagtt tcataagttc   4140
gttagtggtt ccctaaacga aaccttgttt ttctttgcaa tcaacaggtc ccctaaaaat   4200
gcctatgttg aaggtgatgc ctcaagcgca agctatttct tggctggtgc tgcaattact   4260
ggagggactg tgactgtgga aggttgtggc accaccagtt tgcaggtaaa gatttcttgg   4320
ctggtgctac aataactgct tttgtctttt tggtttcagc attgttctca gagtcactaa   4380
ataacattat catctgcaaa tgtcaaatag acatacttag gtgaattcat gtaaccgttt   4440
ccttacaaat ttgctgaaac ctcagggtga tgtgaagttt gctgaggtac tggagatgat   4500
gggagcgaag gttacatgga ccgagactag cgtaactgtt actggcccac cgcgggagcc   4560
```

-continued

```
atttgggagg aaacacctca aggcgattga tgtcaacatg aacaagatgc ctgatgtcgc   4620

catgactctt gctgtggttg ccctctttgc cgatggcccg acagccatca gagacggtaa   4680

aacattctca gccctacaac catgcctctt ctacatcact acttgacaag actaaaaact   4740

attggctcgt tggcagtggc ttcctggaga gtaaaggaga ccgagaggat ggttgcgatc   4800

cggacggagc taaccaaggt aaggctacat acttcacatg tctcacgtcg tctttccata   4860

gctcgctgcc tcttagcggc ttgcctgcgg tcgctccatc ctcggttgct gtctgtgttt   4920

tccacagctg ggagcatctg ttgaggaagg gccggactac tgcatcatca cgccgccgga   4980

gaagctgaac gtgacggcga tcgacacgta cgacgaccac aggatggcca tggccttctc   5040

ccttgccgcc tgtgccgagg tccccgtgac catccgggac cctgggtgca cccggaagac   5100

cttccccgac tacttcgatg tgctgagcac tttcgtcaag aattaataaa gcgtgcgata   5160

ctaccacgca gcttgattga agtgataggc ttgtgctgag gaaatacatt tcttttgttc   5220

tgtttttct ctttcacggg attaagtttt gagtctgtaa cgttagttgt ttgtagcaag   5280

tttctatttc ggatcttaag tttgtgcact gtaagccaaa tttcatttca agagtggttc   5340

gttggaataa taagaataat aaattacgtt tcagtggctg tcaagcctgc tgctacgttt   5400

taggagatgg cattagacat tcatcatcaa caacaataaa accttttagc ctcaaacaat   5460

aatagtgaag ttatttttta gtcctaaaca agttgcatta ggatatagtt aaaacacaaa   5520

agaagctaaa gttagggttt agacatgtgg atattgtttt ccatgtatag tatgttcttt   5580

ctttgagtct catttaacta cctctacaca taccaacttt agtttttttt ctacctcttc   5640

atgttactat ggtgccttct tatcccactg agcattggta tatttagagg tttttgttga   5700

acatgcctaa atcatctcaa tcaacgatgg acaatctttt cttcgattga gctgaggtac   5760

gtcatctaca ggataggacc ttgagaatat gtgtccgtca atagctaacc ctctactaat   5820

tttttcaatc aagcaaccta ttggcttgac tttaattcgt accggcttct actacttcta   5880

cagtattttg tctctataaa ttgcagctac aacagtcaga acggctggct ttaaaatcaa   5940

atggcctaag gatcattgaa aggcatctta gcaatgtcta aaattattac cttctctaga   6000

cgttgatatc                                                          6010
```

```
<210> SEQ ID NO 6
<211> LENGTH: 6010
<212> TYPE: DNA
<213> ORGANISM: Zea mays
<220> FEATURE:
<221> NAME/KEY: misc_feature
<222> LOCATION: (2886)..(2886)
<223> OTHER INFORMATION: substituting thymine for cytosine at position
      2886 as compared to SEQ ID NO: 5
<220> FEATURE:
<221> NAME/KEY: misc_feature
<222> LOCATION: (2897)..(2897)
<223> OTHER INFORMATION: substituting thymine for cytosine at position
      2897 as compared to SEQ ID NO: 5

<400> SEQUENCE: 6

atcgattgca accttcaaat tctcttcgat cttccttcca aattcatcta atatttcatc     60

ctcggcaagg aaatcttcta acgtgtaaac ttcactggga tccaactcga aaggatcaaa    120

ctctccctct ggttcgtttg acattgtgga tggagtgact aacctgctaa caccctgcaa    180

caatttatac aggagcatat cctcatgcac acgcaaaact gatgttgtcc acaagacacg    240

cacaggacac gcacaggaca cgcaaacagt ttcagactca tgcacacgca catcagtttc    300

agactcaggc acacgcacat caaatcacct tcgcttgtcg atgagtcgca gccgcatcgt    360
```

-continued

```
acaatggcga ttttaccgac gataaggcat gggagcacga gccgtcgccg tcgccttgcg    420
agacgacggg agcgatctct cccttcattt aatctcttcc acgtcaggtt attttgctga    480
gatggcagta tacagacggc aaagttaatg ccgttgtaca tgcccttaga ctcttccgtc    540
accaactcac ttagattttt acaacggaac ataaggttcg cttgcagact tacatataag    600
gtatagttgc ataataatcg ccttatgctg tacattgcga cacccgtaaa tattcgatga    660
aatattagta cacaatatta aataagaacg aacaatacat atattatcat tgatcttagt    720
atctcctttt gctcctcgta gaacaattct gtgtaaatta tgcgtaaaat tcgaggacca    780
aaacattggc tagaaaaata cctaaaatca gttttgcaat tgtttctgat tttcctcata    840
ttttcttgct tataaagttt tccaaaagta ccattttgga tgaaaaaacg gaaaacaacg    900
ctggtctact tgtaaatttg gtagtgacat ttgggaccgt ctagacacga cctaaaaata    960
gtagtctaaa acatagtctg acacgatgcc ttaaaaatag acgacaaagc acaacacgat   1020
tagatgtgtc gtgttttgac cgacacgaca caaagtaagg cacgatttaa aacccaataa   1080
ataatatttt aatggttatt ttatgttcca ataattttca tctcttcaaa aaaatgttat   1140
agaaatcatt gatacttagt tgaatatcct aacacaatat atatatatat attaatatat   1200
atatatatca attttaagtc actttgctag acatagtaat atattttaaa tattttctct   1260
ttcttgtata tttttaaaat acacatcagt ttttatatgt gtcgtgcttg aaccgacacg   1320
atataatcat cggttcgccg tacttctaga tcatgatgtt cctaggtttt aatattaaga   1380
gacggtctat attaactcaa aactatttcg tgaaaggcta actcgaaaaa aaaatgaatg   1440
taatcacggc ccgtcctgga ttcgagattc taacgtttca ttcgtgtcca gtgtgcacac   1500
ttgtggaaaa ggaagacgaa gaaaaaaacc aacaactaac tccggcccgc cggatgcgcc   1560
cacctacttc cccctcgccc ctctcatggt ctctctcgcg cccagatctg ctactagacg   1620
gcaccgctgc agcgcgtcgt gtcgcggggg ttggtggcag gcagcgagag cttgccgttc   1680
ctctctctca gttgtcaggt cctaggctca cctcaccggc tcccagcccg cttctatttc   1740
ttcctccccg accccgtgca ggtggcagtc cagtccacgc caccaaccgc gaggcgaacc   1800
aaaccaaccc actctcccca accccgcgcg cccaggccgc ccgccctacc aaccatcggc   1860
gtcggcaatg gcggccatgg cgaccaaggc cgccgcgggc accgtgtcgc tggacctcgc   1920
cgcgccgtcg cgccgccacc accgcccgag ctcggcgcgc ccgcccgccc gccccgccgt   1980
ccgcgggctg cgggcgcctg ggcgccgcgt gatcgccgcg ccgccggcgg cggcagcggc   2040
ggcggcggtg caggcgggtg ccgaggagat cgtgctgcag cccatcaagg agatctccgg   2100
caccgtcaag ctgccggggt ccaagtcgct ttccaaccgg atcctcctgc tcgccgccct   2160
gtccgaggtg agcgattttg gtgcttgctg cgctgccctg tctcactgct acctaaatgt   2220
tttgcctgtc gaataccatg gattctcggt gtaatccatc tcacgatcag atgcaccgca   2280
tgtcgcatgc ctagctctct ctaatttgtc tagtagtttg tatacggatt aatattgata   2340
aatcggtacc gcaaaagcta ggtgtaaata aacactagaa aattggatgt tcccctatcg   2400
gcctgtactc ggctactcgt tcttgtgatg gcatgctgtc tcttcttggt gtttggtgaa   2460
caaccttatg aaatttgggc gcaaagaact cgccctcaag ggttgatctt atgccatcgt   2520
catgataaac agtggagcac ggacgatcct ttacgttgtt tttaacaaac tttgtcagaa   2580
aactagcatc attaacttct taatgacgat ttcacaacaa aaaaaggtaa cctcgctact   2640
aacataacaa aatacttgtt gcttattaat tatatgtttt ttaatctttg atcaggggac   2700
aacagtggtt gataacctgt tgaacagtga ggatgtccac tacatgctcg gggccttgag   2760
```

-continued

```
gactcttggt ctctctgtcg aagcggacaa agctgccaaa agagctgtag ttgttggctg   2820
tggtggaaag ttcccagttg aggattctaa agaggaagtg cagctcttct tggggaatgc   2880
tggaattgca atgcggtcat tgacagcagc tgttactgct gctggtggaa atgcaacgta   2940
tgtttcctct ctttctctct acaatacttg ctggagttag tatgaaaccc atgggtatgt   3000
ctagtggctt atggtgtatt ggtttttgaa cttcagttac gtgcttgatg gagtaccaag   3060
aatgagggag agacccattg gcgacttggt tgtcggattg aagcagcttg gtgcagatgt   3120
tgattgtttc cttggcactg actgcccacc tgttcgtgtc aatggaatcg gagggctacc   3180
tggtggcaag gttagctact aagggccaca tgttacattc ttctgtaaat ggtacaacta   3240
ttgtcgagct tttgcatttg taaggaaagc attgattgat ctgaatttga tgctacacca   3300
caaaatatcc tacaaatggt catccctaac tagcaaacaa tgaagtaata cttggcatgt   3360
gtttatcaaa ttaatttcca tcttctgggg cattgcctgt tttctagtct aatagcattt   3420
gtttttagca ttaattagct cttacaattg ttatgttcta caggtcaagc tgtctggctc   3480
catcagcagt cagtacttga gtgccttgct gatggctgct cctttggctc ttggggatgt   3540
ggagattgaa atcattgata aattaatctc cattccctac gtcgaaatga cattgagatt   3600
gatggagcgt tttggtgtga aagcagagca ttctgatagc tgggacagat tctacattaa   3660
gggaggtcaa aaatacaagt aagctctgta atgtatttca ctactttgat gccaatgttt   3720
cagttttcag ttttccaaac agtcgcatca atatttgaat agatgcactg tagaaaaaaa   3780
atcattgcag ggaaaaacta gtactgagta ttttgactgt aaattatttt accagtcgga   3840
atatagtcag tctattggag tcaagagcgt gaaccgaaat agccagttaa ttatcccatt   3900
atacagagga caaccatgta tactattgaa acttggttta taagagaatc taggtagctg   3960
gactcgtagc tgcttggcat ggataccttc ttatctttag gaaaagacac ttgatttttt   4020
ttttctgtgg ccctctatga tgtgtgaacc tgcttctcta ttgctttaga aggatatatc   4080
tatgtcgtta tgcaacatgc ttcccttagc catttgtact gaaatcagtt tcataagttc   4140
gttagtggtt ccctaaacga aaccttgttt ttctttgcaa tcaacaggtc ccctaaaaat   4200
gcctatgttg aaggtgatgc ctcaagcgca agctatttct tggctggtgc tgcaattact   4260
ggagggactg tgactgtgga aggttgtggc accaccagtt tgcaggtaaa gatttcttgg   4320
ctggtgctac aataactgct tttgtctttt tggtttcagc attgttctca gagtcactaa   4380
ataacattat catctgcaaa tgtcaaatag acatacttag gtgaattcat gtaaccgttt   4440
ccttacaaat ttgctgaaac ctcagggtga tgtgaagttt gctgaggtac tggagatgat   4500
gggagcgaag gttacatgga ccgagactag cgtaactgtt actggcccac cgcgggagcc   4560
atttgggagg aaacacctca aggcgattga tgtcaacatg aacaagatgc ctgatgtcgc   4620
catgactctt gctgtggttg ccctctttgc cgatggcccg acagccatca gagacggtaa   4680
aacattctca gccctacaac catgcctctt ctacatcact acttgacaag actaaaaact   4740
attggctcgt tggcagtggc ttcctggaga gtaaaggaga ccgagaggat ggttgcgatc   4800
cggacggagc taaccaaggt aaggctacat acttcacatg tctcacgtcg tctttccata   4860
gctcgctgcc tcttagcggc ttgcctgcgg tcgctccatc ctcggttgct gtctgtgttt   4920
tccacagctg ggagcatctg ttgaggaagg gccggactac tgcatcatca cgccgccgga   4980
gaagctgaac gtgacggcga tcgacacgta cgacgaccac aggatggcca tggccttctc   5040
ccttgccgcc tgtgccgagg tccccgtgac catccgggac cctgggtgca cccggaagac   5100
cttccccgac tacttcgatg tgctgagcac tttcgtcaag aattaataaa gcgtgcgata   5160
```

-continued

```
ctaccacgca gcttgattga agtgataggc ttgtgctgag gaaatacatt tcttttgttc   5220

tgtttttct ctttcacggg attaagtttt gagtctgtaa cgttagttgt ttgtagcaag   5280

tttctatttc ggatcttaag tttgtgcact gtaagccaaa tttcatttca agagtggttc   5340

gttggaataa taagaataat aaattacgtt tcagtggctg tcaagcctgc tgctacgttt   5400

taggagatgg cattagacat tcatcatcaa caacaataaa accttttagc ctcaaacaat   5460

aatagtgaag ttatttttta gtcctaaaca agttgcatta ggatatagtt aaaacacaaa   5520

agaagctaaa gttagggttt agacatgtgg atattgtttt ccatgtatag tatgttcttt   5580

ctttgagtct catttaacta cctctacaca taccaacttt agtttttttt ctacctcttc   5640

atgttactat ggtgccttct tatcccactg agcattggta tatttagagg tttttgttga   5700

acatgcctaa atcatctcaa tcaacgatgg acaatctttt cttcgattga gctgaggtac   5760

gtcatctaca ggataggacc ttgagaatat gtgtccgtca atagctaacc ctctactaat   5820

tttttcaatc aagcaaccta ttggcttgac tttaattcgt accggcttct actacttcta   5880

cagtattttg tctctataaa ttgcagctac aacagtcaga acggctggct ttaaaatcaa   5940

atggcctaag gatcattgaa aggcatctta gcaatgtcta aaattattac cttctctaga   6000

cgttgatatc                                                          6010
```

```
<210> SEQ ID NO 7
<211> LENGTH: 521
<212> TYPE: PRT
<213> ORGANISM: Arabidopsis thaliana

<400> SEQUENCE: 7

Met Ala Ser Ser Leu Thr Ser Lys Ser Ile Leu Gly Cys Thr Lys Pro
1               5                   10                  15

Ala Ser Ser Ser Phe Leu Pro Ser Glu Leu Arg Arg Leu Ser Ser Pro
            20                  25                  30

Ala Val Gln Ile Ser Leu His Ser Gln Thr Arg Lys Asn Phe Arg Gln
        35                  40                  45

Ser Trp Gly Leu Lys Lys Ser Asp Leu Met Leu Asn Gly Ser Glu Ile
    50                  55                  60

Arg Pro Val Lys Val Arg Ala Ser Val Ser Thr Ala Glu Lys Ala Ser
65                  70                  75                  80

Glu Ile Val Leu Gln Pro Ile Arg Glu Ile Ser Gly Leu Ile Lys Leu
                85                  90                  95

Pro Gly Ser Lys Ser Leu Ser Asn Arg Ile Leu Leu Leu Ala Ala Leu
            100                 105                 110

Ser Glu Gly Thr Thr Val Val Asp Asn Leu Leu Asn Ser Asp Asp Ile
        115                 120                 125

Asn Tyr Met Leu Asp Ala Leu Lys Ile Leu Gly Leu Asn Val Glu Thr
    130                 135                 140

His Ser Glu Asn Asn Arg Ala Val Val Glu Gly Cys Gly Gly Val Phe
145                 150                 155                 160

Pro Ala Ser Ile Asp Ser Lys Ser Asp Ile Glu Leu Tyr Leu Gly Asn
                165                 170                 175

Ala Gly Ile Ala Met Arg Ser Leu Thr Ala Ala Val Thr Ala Ala Gly
            180                 185                 190

Gly Asn Ala Ser Tyr Val Leu Asp Gly Val Pro Arg Met Arg Glu Arg
        195                 200                 205

Pro Ile Gly Asp Leu Val Val Gly Leu Lys Gln Leu Gly Ala Asp Val
    210                 215                 220
```

-continued

```
Glu Cys Thr Leu Gly Thr Asn Cys Pro Pro Val Arg Val Asn Ala Asn
225                 230                 235                 240

Gly Gly Leu Pro Gly Gly Lys Val Lys Leu Ser Gly Ser Ile Ser Ser
                245                 250                 255

Gln Tyr Leu Thr Ala Leu Leu Met Ala Ala Pro Leu Ala Leu Gly Asp
            260                 265                 270

Val Glu Ile Glu Ile Val Asp Lys Leu Ile Ser Val Pro Tyr Val Glu
        275                 280                 285

Met Thr Leu Lys Leu Met Glu Arg Phe Gly Val Ser Ala Glu His Ser
    290                 295                 300

Glu Ser Trp Asp Arg Phe Phe Val Lys Gly Gly Gln Lys Tyr Lys Ser
305                 310                 315                 320

Pro Gly Asn Ala Tyr Val Glu Gly Asp Ala Ser Ser Ala Ser Tyr Phe
                325                 330                 335

Leu Ala Gly Ala Ala Ile Thr Gly Glu Thr Val Thr Val Glu Gly Cys
            340                 345                 350

Gly Thr Thr Ser Leu Gln Gly Asp Val Lys Phe Ala Glu Val Leu Glu
        355                 360                 365

Lys Met Gly Cys Lys Val Ser Trp Thr Glu Asn Ser Val Thr Val Thr
    370                 375                 380

Gly Pro Ser Arg Asp Ala Phe Gly Met Arg His Leu Arg Ala Ile Asp
385                 390                 395                 400

Val Asn Met Asn Lys Met Pro Asp Val Ala Met Thr Leu Ala Val Val
                405                 410                 415

Ala Leu Phe Ala Asp Gly Pro Thr Thr Ile Arg Asp Val Ala Ser Trp
            420                 425                 430

Arg Val Lys Glu Thr Glu Arg Met Ile Ala Ile Cys Thr Glu Leu Arg
        435                 440                 445

Lys Leu Gly Ala Thr Val Glu Glu Gly Ser Asp Tyr Cys Val Ile Thr
    450                 455                 460

Pro Pro Lys Lys Val Lys Pro Ala Glu Ile Asp Thr Tyr Asp Asp His
465                 470                 475                 480

Arg Met Ala Met Ala Phe Ser Leu Ala Ala Cys Ala Asp Val Pro Ile
                485                 490                 495

Thr Ile Asn Asp Pro Gly Cys Thr Arg Lys Thr Phe Pro Asp Tyr Phe
            500                 505                 510

Gln Val Leu Glu Arg Ile Thr Lys His
        515                 520


<210> SEQ ID NO 8
<211> LENGTH: 520
<212> TYPE: PRT
<213> ORGANISM: Arabidopsis thaliana

<400> SEQUENCE: 8

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Ala Ser Glu
65                  70                  75                  80
```

-continued

```
Ile Val Leu Gln Pro Ile Arg Glu Ile Ser Gly Leu Ile Lys Leu Pro
                85                  90                  95

Gly Ser Lys Ser Leu Ser Asn Arg Ile Leu Leu Leu Ala Ala Leu Ser
            100                 105                 110

Glu Gly Thr Thr Val Val Asp Asn Leu Leu Asn Ser Asp Asp Ile Asn
        115                 120                 125

Tyr Met Leu Asp Ala Leu Lys Arg Leu Gly Leu Asn Val Glu Thr Asp
    130                 135                 140

Ser Glu Asn Asn Arg Ala Val Val Glu Gly Cys Gly Gly Ile Phe Pro
145                 150                 155                 160

Ala Ser Ile Asp Ser Lys Ser Asp Ile Glu Leu Tyr Leu Gly Asn Ala
                165                 170                 175

Gly Ile Ala Met Arg Ser Leu Thr Ala Ala Val Thr Ala Ala Gly Gly
            180                 185                 190

Asn Ala Ser Tyr Val Leu Asp Gly Val Pro Arg Met Arg Glu Arg Pro
        195                 200                 205

Ile Gly Asp Leu Val Val Gly Leu Lys Gln Leu Gly Ala Asp Val Glu
    210                 215                 220

Cys Thr Leu Gly Thr Asn Cys Pro Pro Val Arg Val Asn Ala Asn Gly
225                 230                 235                 240

Gly Leu Pro Gly Gly Lys Val Lys Leu Ser Gly Ser Ile Ser Ser Gln
                245                 250                 255

Tyr Leu Thr Ala Leu Leu Met Ser Ala Pro Leu Ala Leu Gly Asp Val
            260                 265                 270

Glu Ile Glu Ile Val Asp Lys Leu Ile Ser Val Pro Tyr Val Glu Met
        275                 280                 285

Thr Leu Lys Leu Met Glu Arg Phe Gly Val Ser Val Glu His Ser Asp
    290                 295                 300

Ser Trp Asp Arg Phe Phe Val Lys Gly Gly Gln Lys Tyr Lys Ser Pro
305                 310                 315                 320

Gly Asn Ala Tyr Val Glu Gly Asp Ala Ser Ser Ala Ser Tyr Phe Leu
                325                 330                 335

Ala Gly Ala Ala Ile Thr Gly Glu Thr Val Thr Val Glu Gly Cys Gly
            340                 345                 350

Thr Thr Ser Leu Gln Gly Asp Val Lys Phe Ala Glu Val Leu Glu Lys
        355                 360                 365

Met Gly Cys Lys Val Ser Trp Thr Glu Asn Ser Val Thr Val Thr Gly
    370                 375                 380

Pro Pro Arg Asp Ala Phe Gly Met Arg His Leu Arg Ala Ile Asp Val
385                 390                 395                 400

Asn Met Asn Lys Met Pro Asp Val Ala Met Thr Leu Ala Val Val Ala
                405                 410                 415

Leu Phe Ala Asp Gly Pro Thr Thr Ile Arg Asp Val Ala Ser Trp Arg
            420                 425                 430

Val Lys Glu Thr Glu Arg Met Ile Ala Ile Cys Thr Glu Leu Arg Lys
        435                 440                 445

Leu Gly Ala Thr Val Glu Glu Gly Ser Asp Tyr Cys Val Ile Thr Pro
    450                 455                 460

Pro Lys Lys Val Lys Thr Ala Glu Ile Asp Thr Tyr Asp Asp His Arg
465                 470                 475                 480

Met Ala Met Ala Phe Ser Leu Ala Ala Cys Ala Asp Val Pro Ile Thr
                485                 490                 495
```

-continued

```
Ile Asn Asp Pro Gly Cys Thr Arg Lys Thr Phe Pro Asp Tyr Phe Gln
            500                 505                 510

Val Leu Glu Arg Ile Thr Lys His
        515                 520


<210> SEQ ID NO 9
<211> LENGTH: 506
<212> TYPE: PRT
<213> ORGANISM: Zea mays

<400> SEQUENCE: 9

Met Ala Ala Met Ala Thr Lys Ala Ala Ala Gly Thr Val Ser Leu Asp
1               5                   10                  15

Leu Ala Ala Pro Ser Arg Arg His His Arg Pro Ser Ser Ala Arg Pro
            20                  25                  30

Pro Ala Arg Pro Ala Val Arg Gly Leu Arg Ala Pro Gly Arg Arg Val
        35                  40                  45

Ile Ala Ala Pro Pro Ala Ala Ala Ala Ala Ala Ala Val Gln Ala Gly
    50                  55                  60

Ala Glu Glu Ile Val Leu Gln Pro Ile Lys Glu Ile Ser Gly Thr Val
65                  70                  75                  80

Lys Leu Pro Gly Ser Lys Ser Leu Ser Asn Arg Ile Leu Leu Leu Ala
                85                  90                  95

Ala Leu Ser Glu Gly Thr Thr Val Val Asp Asn Leu Leu Asn Ser Glu
            100                 105                 110

Asp Val His Tyr Met Leu Gly Ala Leu Arg Thr Leu Gly Leu Ser Val
        115                 120                 125

Glu Ala Asp Lys Ala Ala Lys Arg Ala Val Val Val Gly Cys Gly Gly
    130                 135                 140

Lys Phe Pro Val Glu Asp Ser Lys Glu Glu Val Gln Leu Phe Leu Gly
145                 150                 155                 160

Asn Ala Gly Ile Ala Met Arg Ser Leu Thr Ala Ala Val Thr Ala Ala
                165                 170                 175

Gly Gly Asn Ala Thr Tyr Val Leu Asp Gly Val Pro Arg Met Arg Glu
            180                 185                 190

Arg Pro Ile Gly Asp Leu Val Val Gly Leu Lys Gln Leu Gly Ala Asp
        195                 200                 205

Val Asp Cys Phe Leu Gly Thr Asp Cys Pro Pro Val Arg Val Asn Gly
    210                 215                 220

Ile Gly Gly Leu Pro Gly Gly Lys Val Lys Leu Ser Gly Ser Ile Ser
225                 230                 235                 240

Ser Gln Tyr Leu Ser Ala Leu Leu Met Ala Ala Pro Leu Ala Leu Gly
                245                 250                 255

Asp Val Glu Ile Glu Ile Ile Asp Lys Leu Ile Ser Ile Pro Tyr Val
            260                 265                 270

Glu Met Thr Leu Arg Leu Met Glu Arg Phe Gly Val Lys Ala Glu His
        275                 280                 285

Ser Asp Ser Trp Asp Arg Phe Tyr Ile Lys Gly Gly Gln Lys Tyr Lys
    290                 295                 300

Ser Pro Lys Asn Ala Tyr Val Glu Gly Asp Ala Ser Ser Ala Ser Tyr
305                 310                 315                 320

Phe Leu Ala Gly Ala Ala Ile Thr Gly Gly Thr Val Thr Val Glu Gly
                325                 330                 335

Cys Gly Thr Thr Ser Leu Gln Gly Asp Val Lys Phe Ala Glu Val Leu
            340                 345                 350
```

-continued

```
Glu Met Met Gly Ala Lys Val Thr Trp Thr Glu Thr Ser Val Thr Val
        355                 360                 365

Thr Gly Pro Pro Arg Glu Pro Phe Gly Arg Lys His Leu Lys Ala Ile
    370                 375                 380

Asp Val Asn Met Asn Lys Met Pro Asp Val Ala Met Thr Leu Ala Val
385                 390                 395                 400

Val Ala Leu Phe Ala Asp Gly Pro Thr Ala Ile Arg Asp Val Ala Ser
                405                 410                 415

Trp Arg Val Lys Glu Thr Glu Arg Met Val Ala Ile Arg Thr Glu Leu
            420                 425                 430

Thr Lys Leu Gly Ala Ser Val Glu Glu Gly Pro Asp Tyr Cys Ile Ile
        435                 440                 445

Thr Pro Pro Glu Lys Leu Asn Val Thr Ala Ile Asp Thr Tyr Asp Asp
    450                 455                 460

His Arg Met Ala Met Ala Phe Ser Leu Ala Ala Cys Ala Glu Val Pro
465                 470                 475                 480

Val Thr Ile Arg Asp Pro Gly Cys Thr Arg Lys Thr Phe Pro Asp Tyr
                485                 490                 495

Phe Asp Val Leu Ser Thr Phe Val Lys Asn
            500                 505
```

What is claimed is:

1. A method of making a glyphosate-resistant plant cell, comprising:

(a) introducing a first DNA fragment into a plurality of regenerable plant cells, the first DNA fragment comprising a sequence selected from the group consisting of SEQ ID NO: 2, SEQ ID NO: 4 and SEQ ID NO: 6; and (b) selecting from said regenerable plant cells a glyphosate-resistant plant cell which is stably transformed with the first DNA fragment.

2. The method according to claim 1, further comprising introducing a second DNA fragment with the first DNA fragment into said regenerable plant cells, wherein the second DNA fragment comprises a sequence selected from the group consisting of SEQ ID NO: 1, SEQ ID NO: 4 and SEQ ID NO: 6, and the sequence of the first DNA fragment is different from the sequence of the second DNA fragment.

3. The method according to claim 2, wherein the first DNA fragment comprises SEQ ID NO: 2, and the second DNA fragment comprises SEQ ID NO: 4.

4. A glyphosate-resistant plant cell made according to the method of claim 3, which is stably transformed with said first DNA fragment and said second DNA fragment.

5. A plant regenerated from the glyphosate-resistant plant cell of claim 4.

6. A regenerable, glyphosate-resistant plant cell comprising an introduced, chromosomally integrated DNA sequence which comprises a sequence selected from the group consisting of SEQ ID NO: 2, SEQ ID NO: 4 and SEQ ID NO: 6.

7. The glyphosate-resistant plant cell according to claim 6, comprising another introduced, chromosomally integrated DNA sequence, wherein said another introduced, integrated DNA sequence comprises a sequence selected from the group consisting of SEQ ID NO: 2, SEQ ID NO: 4 and SEQ ID NO: 6.

8. The glyphosate-resistant plant cell according to claim 6, wherein the introduced, chromosomally integrated DNA sequence comprises SEQ ID NO: 2, and wherein the plant cell comprises another introduced, chromosomally integrated DNA sequence which comprises SEQ ID NO: 4.

9. A plant regenerated from the glyphosate-resistant plant cell of claim 6.

10. A plant regenerated from the glyphosate-resistant plant cell of claim 8.

11. An isolated polynucleotide comprising the sequence depicted in SEQ ID NO: 2.

12. An isolated polynucleotide comprising the sequence depicted in SEQ ID NO: 4.

13. An isolated polynucleotide comprising the sequence depicted in SEQ ID NO: 6.

* * * * *